United States Patent
Sutovsky et al.

(10) Patent No.: US 7,741,058 B2
(45) Date of Patent: Jun. 22, 2010

(54) METHODS AND COMPOSITIONS FOR DETECTING SPERMATOZOA OR SEMEN IN A SAMPLE

(75) Inventors: Peter Sutovsky, Columbia, MO (US); Antonio Miranda-Vizuete, Sevilla (ES)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 12/180,290

(22) Filed: Jul. 25, 2008

(65) Prior Publication Data
US 2009/0053717 A1    Feb. 26, 2009

Related U.S. Application Data

(63) Continuation of application No. 11/106,796, filed on Apr. 15, 2005, now Pat. No. 7,485,430.

(60) Provisional application No. 60/562,526, filed on Apr. 15, 2004.

(51) Int. Cl.
*G01N 33/53* (2006.01)
(52) U.S. Cl. .......................................... 435/7.1; 435/7.2
(58) Field of Classification Search ........................ None
See application file for complete search history.

(56) References Cited

U.S. PATENT DOCUMENTS

| 2003/0004402 A1 | 1/2003 | Hitt et al. .................... 600/300 |
| 2005/0282191 A1 | 12/2005 | Sutovsky et al. ............. 435/7.9 |

FOREIGN PATENT DOCUMENTS

| EP | 1 104 808 | 6/2001 |
| WO | WO 98/56909 | 12/1998 |

OTHER PUBLICATIONS

Abaza et al., "Effects of amino acid substitutions outside an antignic site on protein binding to monoclonal antibodies of predetermined specificity obtained by peptide immunization: demonstration with region 145-151 (Antigenic site 5) of myoblobin," *Journal of Protein Chemistry*, 11(5):433-444, 1992.
Abpi-Haila et al., "Mammalian sperm acrosome: formation, contents, and function," *Arch. Biochem. Biophys.*, 379:173-182, 2000.
Arner et al., "Physiological functions of thioredoxin and thioredoxin reductase," *Eur. J. Biochem*, 267(20):6102-6109, 2000.
Baccetti et al., "Apoptosis in human ejaculated sperm cells (notulae seminologicae 9)," *J. Submicrosc. Cytol. Pathol.*, 28:587-596, 1996.
Ballachey et al., "Heterogeneity of sperm nuclear chromatin structure and its relationship to bull fertility," *Biol Reprod.*, 36:915-925, 1987.
Banez et al., "Diagnostic potential of serum proteomic patterns in prostate cancer," *J. of Urology*, 170(2):442-446, 2003.
Bjornstedt et al., "Selenite and selenodiglutathione: reactions with thioredoxin systems," *Methods Enzymol.*, 252:209-219, 1995.
Blobel, "Protein targeting (Nobel lecture)," *Chembiochem.*, 1:86-102, 2000.
Campbell, In: Monoclonal Antibody Technolgy, Campbell et al. (Eds.), Elsevier Science Publishers, Amsterdam-New York-London, pp. 29, 1984.
Coleman et al., "Effects of amino acid sequence changes on antibody-antigen interactions: 55th Forum in immunology: a structural view of immune recognition by antibodies," *Research in Immunology*, 145(1):33-36, 1994.
Cunnea et al., "ERdj5, an endoplasmic reticulum (ER)-resident protein contraining DnaJ and thioredoxin domains, is expressed in secretory cells or following ER stress," *J. Biol. Chem.*, 278(2):1059-1066, 2003.
Douglas-Hamilton,"Validation procedures for the Hamilton Thorne Integrated Visual Optical System sperm and cell analyzer," *Qual. Assur.*, 4:340-347, 1995.
Eklund et al., "Structural and functional relations among thioredoxins of different species," *Proteins*, 11(1):13-28, 1991.
Eliason, "Analysis of semen," In: The Testis, Burger et al., (Eds.), Raven Press, NY, 381-399, 1981.
EMBL Database Accession No. AL158158, dated Sep. 30, 1998.
EMBL Database Accession No. AI188241, dated Oct. 28, 1998.
EMBL Database Accession No. AX975489, dated Jan. 15, 2004.
EMBL Database Accession No. AX971629, dated Jan. 15, 2004.
Evenson et al., "Simultaneous measurement by flow cytometry of sperm cell viability and mitochondrial membrane potential related to cell motility," *J. Histochem. Cytochem.*, 30:279-280, 1982.
Evenson et al., "Utility of the sperm chromatin structure assay as a diagnostic and prognostic tool in the human fertility clinic," *Hum. Reprod.*, 14:1039-1049, 1999.
Ferrari et al., "Chromatin cytophotometric analysis of abnormal bovine spermatozoa," *Andrologia*, 30:85-89, 1998.
Flickinger et al., "Outer dense fiber proteins are dominant postobstruction autoantigens in adult Lewis rats," *Biol. Reprod.*, 64:1451-1459, 2001.
Friedrich, "Genomics and proteomics may help clinicians individualize cancer treatment," *JAMA*, 287(22):2931-2932, 2002.
Fujii et al., "Augmented expression of peroxiredoxin VI in rat lung and kidney after birth implies and antioxidative role," *Eur. J. Biochem.*, 268:218-225, 2001.
Garner et al., "Organelle-specific probe JC-1 identifies membrane potential differences in the mitochondrial function of bovine sperm," *Mol. Reprod. Dev.*, 53:222-229, 1999.
Gjertsen et al., "Analysis of acute myelogenous leukemia: preparation of samples for genomic proteomic analyses," *J. of Hematotherapy and Stem Cell Research*, 11:469-481, 2002.
Guzick et al., "Sperm morphology, motility, and concentration in fertile and infertile men," *N. Engl. J. Med.*, 345:1388-1393, 2001.
Hirota et al., "Thioredoxin superfamily and thioredoxin-inducing agents," *Ann N Y Acad. Sci.*, 957:189-199, 2002.
Holmgren, "Enzymatic reduction-oxidation of protein disulfides by thioredoxin," *Methods Enzymol.*, 107:295-300, 1984.
Hosoda et al., "JPDI, a novel endoplasmic reticulum-resident protein containing both a BiP-interacting J-domain and thioredoxin-like motifs," *J. Biol. Chem.*, 278(4):2669-2676, 2003.

(Continued)

*Primary Examiner*—Jacob Cheu
(74) *Attorney, Agent, or Firm*—Sonnenschein Nath & Rosenthal LLP

(57) ABSTRACT

The present invention concerns compositions and methods for evaluating fertility in humans and animals. The invention may also be used to identify reproductive cancers such as testicular cancer. In various embodiments of the invention, an Sptrx-3 enzyme is used as a fertility marker. Sptrx-3 may be detected in accordance with the invention in vitro or in vivo.

9 Claims, 10 Drawing Sheets

OTHER PUBLICATIONS

Hughes et al., "Human sperm DNA integrity assessed by the comet and ELISA assays," *Mutagenesis*, 14:71-75, 1999.

Jimenez et al., "Cloning, expression and characterization of mouse spermatid specific thioredoxin-1 gene and protein," *Mol. Hum. Reprod.*, 8(8):710-718, 2002.

Jimenez et al., "Purification and characterization of Delta3Trx-1, a splicing variant of human thioredoxin-1 lacking exon 3," *Protein Expression and Purification*, 27(2):319-324, 2003.

Jimenez et al., "Spermatid-specific thioredoxin-3, a novel Golgi apparatus-associated thioredoxin, is a specific marker of aberrant spermatogenesis," *Free Radic. Biol. Med*, 36(1):S81, 2004. And: 12th Biennial Meeting of the Society for Free Radical Research International, Buenos Aires, Argentina, Abstract p. 5-69, May 5-9, 2004.

Jimenez et al., "Spermatocyte/spermatid-specific thioredoxin-3, a novel golgi apparatus-associated thioredoxin, is a specific marker of aberrant spermatogenesis," *J. Biol. Chem.*, 279(33):34971-34982, 2004.

Jorgensen et al., "Semen analysis performed by different laboratory teams: an intervariation study," *Int. J. Androl.*, 20:201-208, 1997.

Kong et al., "A high-resolution recombination map of the human genome," *Nat. Genet.*, 31:241-247, 2002.

Krause, "Computer assisted semen analysis systems: comparison with routine evaluation and prognostic value in male fertility and assisted reproduction," *Hum. Reprod.*, 10(Suppl 1):60-66, 1995.

Kruger et al., "New method of evaluating sperm morphology with predictive value for human in vitro fertilization," *Urology*, 30:248-251, 1987.

Lederman et al., "A single amino acid substitution in a common African allele of the CD4 molecule ablates binding of the monoclonal antibody, OKT4," *Molecular Immunology*, 28:1171-1181, 1991.

Lee et al., "Purification, molecular cloning, and characterization of TRP32, a novel thioredoxin-related mammalian protein of 32kDa," *J. Biol. Chem.*, 273(30):19160-19166, 1998.

Li et al., "Beta-endorphin omission analogs: dissociation of immunoreactivity from other biological activities," *Proc. Natl Acad. Sci. USA*, 77:3211-3214, 1980.

Maggio et al., "Enzyme as immunochemical labels," In: Enzyme-Immunoassay, Maggio et al. (Eds.), CRC Press, 2000.

Miranda-Visuete et al., "The mammalian testis-specific thioredoxin system," *Antioxid Redox Signal*, 6(1):25-40, 2004.

Miranda-Visuete et al., "The mitochondrial Thioredoxin system," *Antioxid Redox Signal*, 2(4):801-810, 2000.

Miranda-Vizuet et al., "Cloning and developmental analysis of murid spermatid-specific thioredoxin-2 (SPTRX-2), a novel sperm fibrous sheath protein and autoantigen," *J. Biol. Chem.*, 278:44874-44885, 2003.

Miranda-Vizuete et al., "Characterization of Sptrx a novel member of the thioredoxin family specifically expressed in human spermatozoa," *J. Biol. Chem.*, 276(34):31567-31574, 2001.

Miranda-Vizuete et al., "Molecular cloning and expression of a cDNA encoding a human thioredoxin-like protein," *Biochem Biophys Res. Commun.*, 243(1):284-288, 1998.

Nickel, "The mystery of nonclassical proteing secretion. A current view on cargo proteins and potential export routes," *Eur. J. Biochem.*, 270:2109-2119, 2003.

Ohta et al., "Identification and characterization of GCP16, a novel acylated Golgi protein that interacts with GCP170," *J. Biol. Chem.*, 278(51):51957-51967, 2003.

Petricoin et al., "Clinical applications of proteomics: proteomic pattern diagnostics," *J. of Mammary Gland Biology Neoplasia*, 7(4):433-440, 2002.

Petricoin et al., "Use of proteomic patterns in serum to identify ovarian cancer," *Lancet*, 359:572-577, 2002.

Ramalho-Santos et al., "Control of membrane fusion during spermiogenesis and the acrosome reaction," *Biol. Reprod.*, 67:1043-1051, 2002.

Rawe et al., "Sperm ubiquitination in patients with dysplasia of the fibrous sheath," *Hum. Reprod.*, 17:2119-2127, 2002.

Rubartelli et al., "Secretion of thioredoxin by normal and neoplastic cells through a leaderless secretory pathway," *J. Biol. Chem.*, 267:24161-24164, 1992.

Sadek et al., "Characterization of human thioredoxin-like 2. A novel microtubule-binding thioredoxin expressed predominantly in the cilia of lung airway epithelium and spermatid manchette and axoneme," *J. Biol. Chem.*, 278(15):13133-13142, 2003.

Sadek et al., "Sptrx-2, a fusion protein composed of one thioredoxin and three tandemly repeated NDP-kinase domains is expressed in human testis germ cells," *Genes Cells*, 6:1077-1090, 2001.

Sasagawa et al., "Possible involvement of the membrane-bound form of peroxiredoxin 4 in acrosome formation during spermiogenesis of rats," *Eur. J. Biochem.*, 268:3053-3061, 2001.

Spyrou et al., "A genome-wide survey of human thioredoxin and glutaredoxin family pseudogenes," *Hum. Genet.*, 109:429-439, 2001.

Spyrou et al., "Cloning and expression of novel mammalian thioredoxin," *J. Biol. Chem.*, 272:2936-2941, 1997.

Sun et al., "Detection of deoxyribonucleic acid fragmentation in human sperm: correlation with fertilization in vitro," *Biol. Reprod.*, 56:602-607, 1997.

Sun et al., "Selenoprotein oxidoreductase with specificity for thioredoxin and glutathione systems," *Proc. Natl. Acad. Sci. USA*, 98:3673-3678, 2001.

Sutovsky et al., "Ubiquitin-based sperm assay for the diagnosis of male factor infertility," *Hum. Reprod.*, 16:250-258, 2001.

Sutovsky et al., "Ubiquitin-dependent sperm quality control mechanism recognizes spermatozoa with DNA defects as revealed by dual ubiquitin-TUNEL assay," *Mol. Reprod. Dev.*, 61:406-413, 2002.

Thompson et al., "CLUSTAL W: improving the sensitivity of progressive multiple sequence alignment through sequence weighting, position-specific gap penalties and weight matrix choice," *Nucleic Acids. Res.*, 22(22):4673-4680, 1994.

van der Schans et al, "An immunochemical assay to detect DNA damage in bovine sperm," *J. Androl.*, 21 250-257. 2000.

Wollman et al., "Cloning and expression of a cDNA for human thioredoxin," *J. Biol. Chem.*, 263:15506-15512, 1988.

World Health Organization (WHO)—Laboratory manual for the examination of human semen and semen cervical mucus interaction. Cambridge University Press, Cambridge, 1987.

World Health Organization (WHO)—Laboratory manual for the examination of human semen and semen cervical mucus interaction. Cambridge University Press, Cambridge, 1992.

World Health Organization (WHO)—Laboratory manual for the examination of human semen and semen cervical mucus interaction. Cambridge University Press, Cambridge, 1999.

Yu et al., "Developmental expression of spermatid-specific thioredoxin-1 protein: transient association to the longitudinal columns of the fibrous sheath during sperm tail formation," *Biol.Reproduction*, 67:1546-1554, 2002.

Office Action regarding U.S. Appl. No. 11/106,796, dated Jan. 24, 2006.

Response to Restriction Requirement regarding U.S. Appl. No. 11/106,796, dated Feb. 24, 2006.

Office Action regarding U.S. Appl. No. 11/106,796, dated May 10, 2006.

Amendment and Response to Office Action regarding U.S. Appl. No. 11/106,796, dated Oct. 10, 2006.

Office Action regarding U.S. Appl. No. 11/106,796, dated Dec. 10, 2006.

Amendment and Response to Office Action regarding U.S. Appl. No. 11/106,796, dated Jun. 1, 2007.

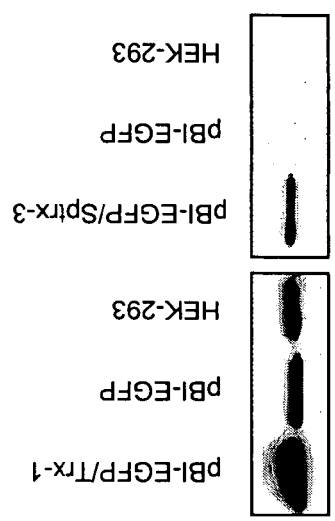
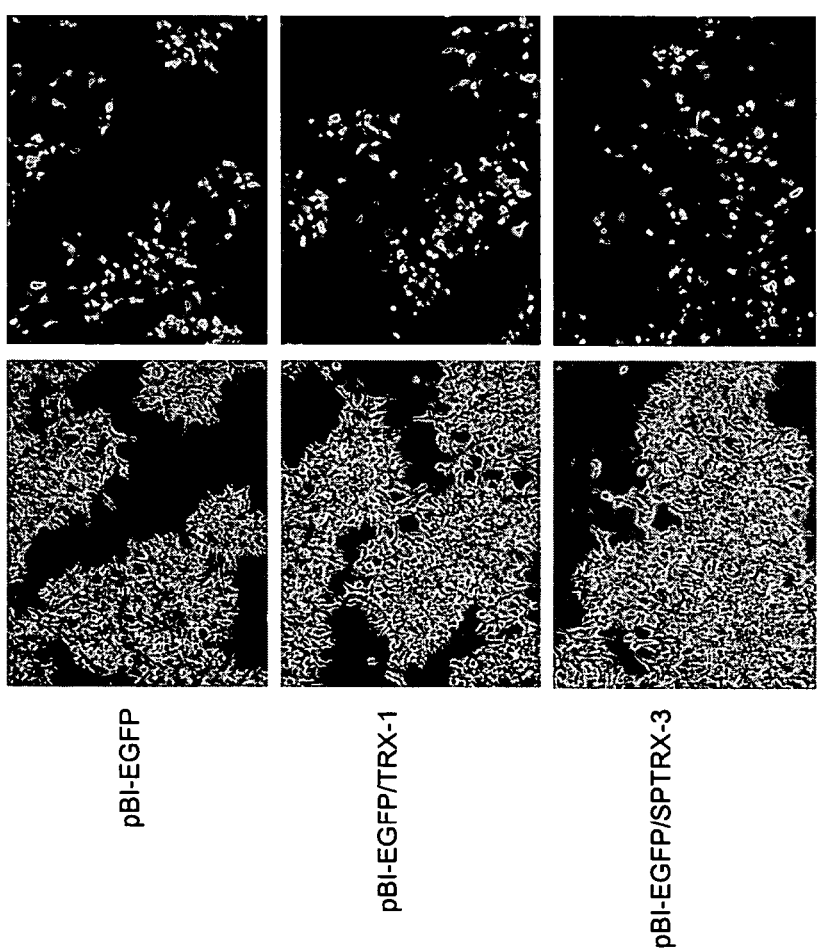
FIG. 7

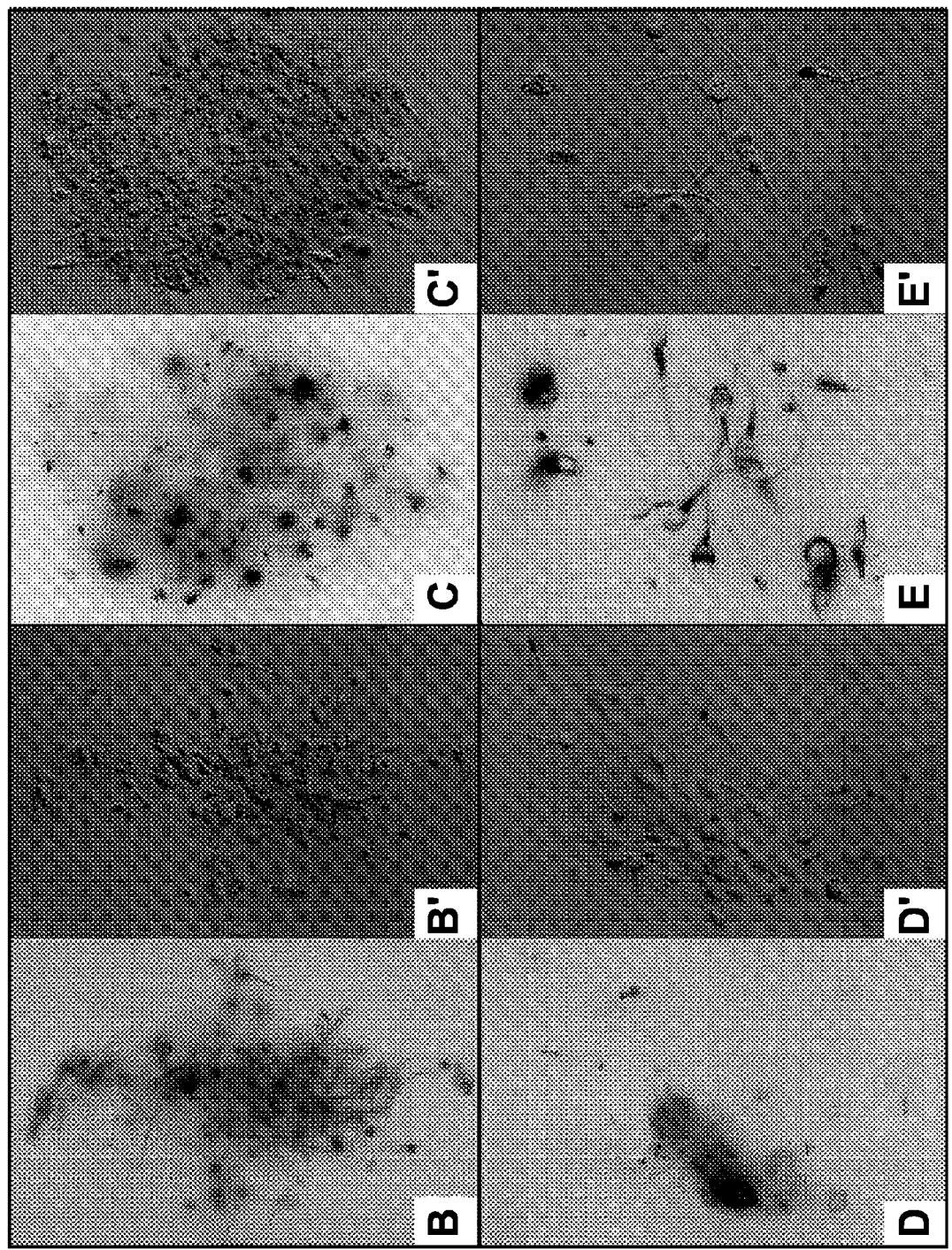
FIG. 8B-E

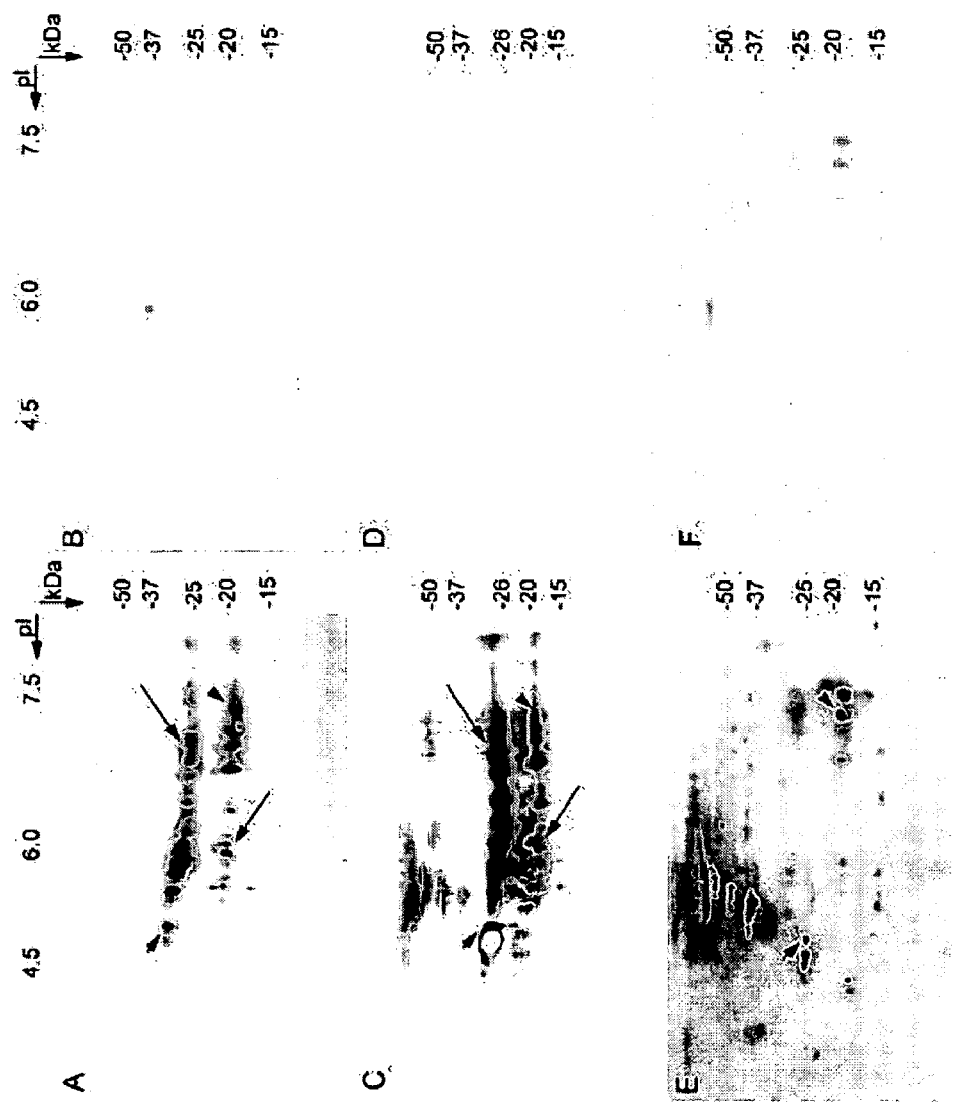
FIGS. 9A-F

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic Primer -continued

<400> SEQUENCE: 1
gaggcctggt gtaatcatgg tacag                                              25

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
caacagggga ttttcatcag cacttc                                             26

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cgagtttgtg tccggcagct gtc                                                23

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctgtaccatg attacaccag gcctc                                              25

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Val Gln Ile Ile Lys Asp Thr Asn Glu Phe Lys Thr Phe Cys
 1               5                  10                  15

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Val Thr Leu Phe Ser Arg Ile Lys Arg Ile Ile Cys
 1               5                  10

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic

```
                    Primer

<400> SEQUENCE: 7
gaggacgcgt gccaccatgg tacagattat taaag                              35

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
cttggctagc ttattacatt aattcttgag                                    30

<210> SEQ ID NO 9
<211> LENGTH: 857
<212> TYPE: DNA
<213> ORGANISM: Homo sapiens

<400> SEQUENCE: 9
atgtattcca ggcaggatac tgtaataaat aggagacagc tacagtgatc caactaaacc    60
aacaggggat tttcatcagc acttccctgg tgtaatcatg gtacagatta ttaaagacac   120
gaatgaattt aaaacatttt tgacagctgc cggacacaaa ctcgcagtgg ttcaattttc   180
ttcgaaacgg tgtggtccct gcaaaaggat gtttcctgtt ttccatgcta tgtctgtgaa   240
ataccaaaat gtattttttg ctaatgtgga tgtgaacaat tctccggagc tggctgaaac   300
ttgtcacatc aaaacaatac ccacatttca gatgttcaag aaaagccaga aggtaaccct   360
attctcaaga atcaaaagaa taatttgctg ttatagaagt ggattcatga gcaacctgat   420
ttttgagttt tgtggagccg atgctaaaaa attggaagcc aagactcaag aattaatgta   480
agctgatctc caaggcaaaa tacacttgtg acatttgaaa aggcaagagc aaatgtgttt   540
gtgctttcat ttccagcaaa tactgtagtg ttccactggt ctctctccta atgctttgct   600
ggttgaatac cataatgcaa tctcactgca caattgctaa aaactgttgc aatatgagag   660
attgcatcat ttccattctc caacttgggc ttcccacttg ctctgagcac actccttggg   720
cagtgttttt atgaccttca caagagaggt cctgcacagc taagtattac caggtcatca   780
agattttcca gagattagca agatccaatt cttcccagt ggtcaaggaa caaataaatg   840
tcttagtgcc ctcgtgc                                                 857

<210> SEQ ID NO 10
<211> LENGTH: 127
<212> TYPE: PRT
<213> ORGANISM: Homo sapiens

<400> SEQUENCE: 10

Met Val Gln Ile Ile Lys Asp Thr Asn Glu Phe Lys Thr Phe Leu Thr
  1               5                  10                  15

Ala Ala Gly His Lys Leu Ala Val Val Gln Phe Ser Ser Lys Arg Cys
                 20                  25                  30

Gly Pro Cys Lys Arg Met Phe Pro Val Phe His Ala Met Ser Val Lys
             35                  40                  45

Tyr Gln Asn Val Phe Phe Ala Asn Val Asp Val Asn Asn Ser Pro Glu
         50                  55                  60

Leu Ala Glu Thr Cys His Ile Lys Thr Ile Pro Thr Phe Gln Met Phe
 65                  70                  75                  80
```

```
Lys Lys Ser Gln Lys Val Thr Leu Phe Ser Arg Ile Lys Arg Ile Ile
                85                  90                  95

Cys Cys Tyr Arg Ser Gly Phe Met Ser Asn Leu Ile Phe Glu Phe Cys
            100                 105                 110

Gly Ala Asp Ala Lys Lys Leu Glu Ala Lys Thr Gln Glu Leu Met
        115                 120                 125
```

<210> SEQ ID NO 11
<211> LENGTH: 127
<212> TYPE: PRT
<213> ORGANISM: Mus musculus

<400> SEQUENCE: 11

```
Met Val Lys Arg Ile Lys Asn Met Ser Glu Leu Lys Glu Leu Phe Ser
 1               5                  10                  15

Asp Ala Gly Asn Lys Leu Val Val Glu Phe Ser Ala Lys Trp Cys
                20                  25                  30

Gly Pro Cys Lys Thr Ile Ala Pro Val Phe Gln Ala Met Ser Leu Lys
            35                  40                  45

Tyr Gln Asn Val Thr Phe Ala Gln Val Asp Val Asp Ser Ser Lys Glu
        50                  55                  60

Leu Ala Glu His Cys Asp Ile Thr Met Leu Pro Thr Phe Gln Met Phe
 65                 70                  75                  80

Lys Tyr Thr Gln Lys Val Thr Pro Phe Ser Arg Leu Lys Arg Val Leu
                85                  90                  95

Cys Cys Leu Arg Ser Gly Pro Lys Ser Lys Met Ile Phe Glu Cys His
            100                 105                 110

Gly Ala Asp Ala Lys Gln Leu Glu Lys Lys Ile Gln Glu Leu Met
        115                 120                 125
```

<210> SEQ ID NO 12
<211> LENGTH: 127
<212> TYPE: PRT
<213> ORGANISM: Rattus rattus

<400> SEQUENCE: 12

```
Met Val Gln Lys Ile Lys Ser Met Arg Glu Phe Lys Glu Leu Leu Gly
 1               5                  10                  15

Ala Ala Gly Asn Arg Leu Val Val Val Glu Phe Ser Ala Gln Trp Cys
                20                  25                  30

Gly Pro Cys Lys Met Ile Ala Pro Ala Phe Gln Ala Met Ser Leu Gln
            35                  40                  45

Tyr Arg Asn Val Met Phe Ala Gln Val Asp Val Asp Ser Ser Gln Glu
        50                  55                  60

Leu Thr Glu His Cys Ser Ile Gln Val Val Pro Thr Phe Gln Met Phe
 65                 70                  75                  80

Lys His Ser Arg Lys Val Thr Pro Phe Ser Arg Leu Lys Arg Ile Leu
                85                  90                  95

Cys Cys Phe Arg Ser Gly Pro Gly Ser Lys Lys Ile Phe Glu Phe Gln
            100                 105                 110

Gly Ala Asp Ile Glu Lys Leu Glu Glu Lys Ile Gln Glu Leu Met
        115                 120                 125
```

<210> SEQ ID NO 13
<211> LENGTH: 105
<212> TYPE: PRT
<213> ORGANISM: Homo sapiens

```
<400> SEQUENCE: 13

Met Val Lys Gln Ile Glu Ser Lys Thr Ala Phe Gln Glu Ala Leu Asp
 1               5                  10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Cys Gln Asp
    50                  55                  60

Val Ala Ser Glu Cys Glu Val Lys Cys Thr Pro Thr Phe Gln Phe Phe
 65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
atggtacaga ttattaaaga c                                                21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gacagctgcc ggacacaaac tcg                                              23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
gtggatgtga acaattctcc gg                                               22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
gaagtggatt catgagcaac ctg                                              23
```

METHODS AND COMPOSITIONS FOR DETECTING SPERMATOZOA OR SEMEN IN A SAMPLE

This application is a Continuation of U.S. application Ser. No. 11/106,796, filed Apr. 15, 2005 now U.S. Pat. No. 7,485,430, which is turn claims the benefit of U.S. Provisional Application Ser. No. 60/562,526, filed Apr. 15, 2004, each of which are specifically incorporated herein by reference in their entirety.

This invention was made with United States government funds under Grant/Contract No. 2002-02069 awarded by the USDA and Grant/Contract No. 2002-35203-12237 awarded by CSREES. The United States government has certain rights in this invention.

INCORPORATION-BY-REFERENCE OF SEQUENCE LISTING IN COMPUTER READABLE FORM

The Sequence Listing, which is a part of the present disclosure, includes a computer readable form 9 kb file entitled "UVMO033US CONT SEQ LIST.txt" comprising nucleotide and/or amino acid sequences of the present invention submitted via EFS-Web. The subject matter of the Sequence Listing is incorporated herein by reference in its entirety.

BACKGROUND OF THE INVENTION

A. Field of the Invention

The present invention relates generally to the field of biology. More particularly, it concerns fertility assays and associated compositions.

B. Description of Related Art

An estimated 20-25% of couples currently seeking infertility treatment are diagnosed with idiopathic or unexplained infertility, where approximately half of those cases are due to male infertility. While many diagnostic options have been developed to evaluate female infertility, male infertility lacks a truly objective semen assay capable of detecting a wide array of both visible and cryptic sperm abnormalities. Consequently, there is a great demand for an accurate and objective means of semen analysis (Amann, 1989) that would be superior to the useful, yet somewhat limited subjective techniques based on strict morphology standards (Kruger et al., 1987; WHO, 1987, 1992, 1999).

The evaluation of sperm motility and morphology as an indicator of infertility has significant limitations (Eliasson, 2003). Automated semen analyses such as CASA and IVOS (Douglas-Hamilton, 1995; Krause, 1995) have been developed for clinical use based on measurements of sperm motility and morphology. Motility is, however, a variable sperm characteristic that declines rapidly after sample donation and depends largely on the length of time between collection and evaluation (typically up to 2 hours post collection; Drobnis, 1992, Eliason, 1981, Jorgensen et al., 1997). While there is a significant overlap between semen parameters of fertile and infertile men, sperm morphology is thought to be a stronger infertility predictor than sperm motility (Guzick et al., 2001).

Other techniques also have significant limitations for evaluation of male fertility. Membrane permeant nuclear stains (Garner and Thomas, 1999) and vital mitochondrial dyes (Evenson et al., 1982; Garner and Thomas, 1999) may be used to discriminate between live and dead spermatozoa. Terminal deoxynucleotidyl transferase-mediated, dUTP nick-end labeling (TUNEL), ELISA or Comet assays are suggestive of the apoptotic or necrotic process in spermatozoa and can be used to screen for DNA strand breaks in some defective spermatozoa (Baccetti et al., 1996; Hughes et al., 1999; Sun et al., 1997; van der Schans et al., 2000). DNA-specific dyes applied to intact (Ferrari et al., 1998) or denatured (SCSA; Ballachey et al., 1987) bull sperm correlate with fertility, but may not correlate well with the results of microscopic semen analysis (Evenson et al., 1999). Chromatin-based assays provide useful information about sperm quality, though they may not cover the whole spectrum of sperm head and tail abnormalities found in both fertile and subfertile semen samples (Sutovsky et al., 2001b; 2002). Thus, a need exists for the creation of an accurate and objective means of semen analysis.

SUMMARY OF THE INVENTION

The invention overcomes the limitations of the prior art by providing novel methods and compositions for the detection of infertility. As described above, there is a need for improved methods of evaluating fertility and diagnosing infertility. The invention therefore provides methods of ascertaining fertility of a sample of spermatozoa, as well as a subject, by detecting the presence and/or activity of the novel fertility marker Sptrx-3, or the presence of antibodies against it in the blood serum of infertile patients. The inventors have demonstrated that an elevation of Sptrx-3 presence and/or activity in association with a sample of spermatozoa is correlated with decreased fertility. Additionally, elevation of Sptrx-3 presence and/or activity in association with a sample of spermatozoa is also correlated with other pathologies including early stages of testicular cancer and autoimmune infertility. Such levels may be evaluated as "elevated" or "increased" by comparison to control samples to establish and average or baseline for the population of subjects. A greater presence of Sptrx-3 relative to an average subject within a population, including a concentration that is in at least about the $60^{th}$, $70^{th}$, $80^{th}$, $90^{th}$, $95^{th}$ and $99^{th}$ percentile of concentration relative to fertile male subjects in the species being examined may be used to assess fertility. In one embodiment, identification of changes in spermatozoa expression and/or function of Sptrx-3 may be used to identify male infertility.

An aspect of the present invention involves an isolated Sptrx-3 polypeptide comprising at least 90% sequence identity to the amino acid sequence of SEQ ID NO:10. In certain embodiments, the polypeptide may comprise the amino acid sequence of SEQ ID NO:10. Some embodiments involve an immunogenic fragment of the isolated Sptrx-3 polypeptide. Certain embodiments involve an antibody or fragment thereof that binds immunologically to said isolated Sptrx-3 polypeptide. Certain embodiments or the present invention involve an isolated nucleic acid sequence selected from the group consisting of: (a) a nucleic acid encoding the polypeptide of claim 1; (b) a nucleic acid that hybridizes to SEQ ID NO:9 under conditions of about 0.1 M NaCl and about 50° C.; (c) a nucleic acid having at least 90% sequence identity to SEQ ID NO:9; and (d) a complement of a nucleic acid of (a), (b), or (c). Certain embodiments involve a probe or primer comprising at least 20 contiguous base pairs of the isolated nucleic acid sequence. Some embodiments of the present invention involve an isolated nucleic acid sequence that hybridizes to SEQ ID NO:9 or a complement thereof under high stringency conditions.

Another aspect of the present invention relates to methods for evaluating the fertility of a subject. Some embodiments involve a method of evaluating the fertility or semen quality of a sample of spermatozoa comprising detecting the content and/or activity of Sptrx-3 in the sample, wherein an increased content and/or activity of Sptrx-3 relative to a control sample is associated with decreased fertility. The method may comprise detecting the presence of antibodies that immunologically bind Sptrx-3, wherein an increased content and/or activity of antibodies that immunologically bind Sptrx-3 relative to a control sample is associated with decreased fertility. Detecting may be done by Western blot analysis, immunocytochemistry, or electron microscopy utilizing colloidal gold particles. The sample of spermatozoa may be from a head of cattle, pig, goat, sheep, horse, mouse, rat, guinea pig, rabbit, dog or cat. In a preferred embodiment, the sample of spermatozoa is from a human. Detecting may comprise immunologic detection, and immunologic detection may comprise detection with polyclonal antisera, autoimmune sera, or a monoclonal antibody preparation. ELISA, RIA and Western blot techniques may also be used for immunologic detection. Said ELISA may be a sandwich ELISA comprising binding of Sptrx-3 to a first antibody preparation fixed to a substrate and a second antibody preparation labeled with an enzyme. Said enzyme may be alkaline phosphatase or horseradish peroxidase. Detection may comprise detection of mRNA. In some embodiments, detecting may comprise detecting a product and/or substrate of Sptrx-3.

The present invention also provides methods of evaluating fertility of a subject, wherein the sample of spermatozoa is obtained from the subject, and wherein the results of the detecting are used to evaluate the fertility of the subject. This method may comprise detecting the content and/or activity of Sptrx-3 in at least two samples of spermatozoa from the subject. In some embodiments, the methods of evaluating fertility may comprise evaluating fertility of a plurality of samples of spermatozoa comprising detecting the content and/or activity of Sptrx-3 in the samples; in some embodiments it may be desirable to select at least one sample of spermatozoa from the plurality of samples based on the results of said detecting for use in artificial insemination or in vitro fertilization.

Another aspect of the present invention relates to a method of in vitro fertilization and/or artificial insemination comprising screening at least one sample of spermatozoa for Sptrx-3 content and/or activity and selecting a sample of spermatozoa for in vitro fertilization and/or artificial insemination based on said screening, wherein increased Sptrx-3 content and/or activity relative to a control subject is associated with decreased fertility.

In certain embodiments, identification of alterations in the expression and/or function of Sptrx-3 in spermatozoa may be used to identify an early stage of cancer. The present invention provides a method of identifying a pre-invasive stage of cancer comprising detecting the content and/or activity of Sptrx-3 in a sample comprising semen or spermatozoa, wherein an increased content and/or activity of Sptrx-3 relative to a control sample is associated with decreased fertility. The sample, in a preferred embodiment, is from a human. In certain embodiments, the pre-invasive stage of cancer is CIS or gonadoblastoma.

Another aspect of the present invention relates to a kit comprising: a first antibody preparation that binds immunologically to Sptrx-3, and a suitable container means thereof. The first antibody may be a monoclonal antibody or a polyclonal antibody. The antibody preparation may be attached to a support, such as a polystyrene plate, test tube or dipstick. In certain embodiments, the kit further comprises at least a second antibody preparation. The second antibody preparation may comprise a detectable label, such as a a fluorescent tag, a chemiluminescent tag and an enzyme. In certain embodiments, the enzyme is alkaline phosphatase or horseradish peroxidase. The kit may further comprise a substrate for said enzyme. The kit may further comprising a buffer or diluent and a suitable container means therefor.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Alignment of the predicted amino acid sequences of human Trx-1 (hTRX-1; SEQ ID NO:13), human Sptrx-3 (hSPTRX-3; SEQ ID NO:10), mouse Sptrx-3 (mSptrx-3; SEQ ID NO:11), and rat Sptrx-3 (rSptrx-3; SEQ ID NO:12) proteins. The alignment was performed using the W-CLUSTAL program included in the DNAStar package (Thompson et al., 1994). Identical residues are shadowed and the thioredoxin active site is boxed. Cysteine residues are marked with a star and the arrow point out the arginine residue in the human Sptrx-3 thioredoxin active site. Conserved amino acids (referred to as Trx-1, (Eklund et al., 1991)) essential for correct folding or function, apart of the active site, are marked with a circle. Sequences of the peptides used for rabbit immunizations are underlined.

FIG. 2A, Comparative exon organization between human Trx-1 and the five different human Sptrx-3 isoforms identified. The exon organization is identical for the first four exons preceding Sptrx-3 exon V, which is not present in Trx1 sequence. The coding sequence in the sixth Sptrx-3 exon still shows high identity with fifth Trx-1 exon. The main difference between the two isoforms of exon VI is the length of the 3'-UTR regions. FIG. 2B, PCR amplification of the different human Sptrx-3 ORF isoforms identified.

FIG. 3A, Human Multiple Tissue Northern blot. Human Sptrx-3 probe hybridized with one mRNA species at 0.9 kb only in testis. β-actin was used as control. FIG. 3B, In dipped sections of adult mouse testis strongest signal (epipolarization signal seen as white grains) can be identified in the middle part of the seminiferous epithelium while rest of the tubule and labeling of the interstitial Leydig cells (Lc) did not exceed background. Bar, 50 μm. FIG. 3C In situ hybridization in mouse testis sections studied at different ages shows the presence of Sptrx-3 mRNA in testis from 3 weeks of age to adult but not in pre-pubertal testis (2 weeks) or liver used as negative control tissue.

FIG. 4A, IHC (Human Immunohistochemistry). FIG. 4B, Rat seminiferous tubules in stages II and VII of the cycle immunoperoxidase-stained with anti-Sptrx-3 antibody. In Stage II the Golgi apparatus (GA) of step 2 round spermatids (RS) is immuno-reactive and is in a juxta-nuclear (N) position associated with the formation of the acrosome. Elongated spermatids (ES) show no immuno-reactivity. In stage VII the immuno-reactive Golgi apparatus of a step 7 round spermatid has dissociated from the newly assembled acrosome (see GA-RS in white font). Further below, larger immuno-reactive Golgi Apparatus (GA) of pachytene (P) spermatocytes can be seen. The residual bodies (RB), appear dark as they absorb the methylene blue counterstain—they are not immuno-reactive. Bar, 10 μm. FIG. 4C, Rat seminiferous tubules in stage XII. The Golgi apparatus (white arrows) of late pachytene spermatocytes (P) is immuno-reactive to anti-Sptrx-3 antibody. The Golgi apparatus of step 12 elongated spermatids (ES) does not appear to be immuno-reactive. Bar, 10 μm. FIG. 4D, Mouse isolated secondary spermatocytes express Sptrx-3 in association with the acrosomal granule.

FIG. 6A, Western-blot analysis of different human protein extracts. Note that "sperm B" sample shows a complete different pattern after a freezing step and that the signal is exclusively detected in sperm samples. FIG. 6B, Same sperm samples used before are compared with testis protein extracts from bovine, mouse, rat and human. The specific amount of protein loaded in each lane is indicated above.

FIG. 7: Human Sptrx-3 was over-expressed in HEK 293 cells bi-directionally with GFP protein as an internal control of transfection/expression (left panel). Five μg of protein extracts from each transfection plate were analyzed by western-blot with anti-TRX-1 or anti-Sptrx-3 antibodies to check TRX-1 and Sptrx-3 over-expression respectively (right upper panel). Finally, 5 μg of each protein extract were used in the thioredoxin enzymatic assay (lower right panel). NADPH and thioredoxin reductase were used as electron donors. The reaction was initiated by adding 1 μg of calf thymus thioredoxin reductase (50 $A_{412}$ units) and stopped after 20 min by the addition of 6M guanidine HCl, 1 mM 5,5'-dithiobis (nitrobenzoic acid). Bar charts show $A_{412}$ of each protein extract. Values are the average of four different experiments performed in triplicate.

FIGS. 8A-E: Sptrx-3 is over-expressed in the spermatozoa of infertile, teratospermic men. FIG. 8A, Dual flow cytometric analysis of Sptrx-3 and sperm quality marker ubiquitin in a semen sample from fertile donor (left column), and an infertile, teratospermic patient (center). Blank, negative control sample (right column) was generated using semen sample from the same fertile donor as shown in left column. Top row shows histograms and median values of relative fluorescence in samples processed with anti-Sptrx-3 serum and an appropriate fluorescently conjugated secondary antibody; middle row shows histograms and medians of the same subjects' sperm samples processed with anti-ubiquitin antibodies. An empty curve in the 'patient' and 'blank' histograms represent the histogram of fertile donor. Bottom row shows scatter diagrams of visible light, illustrating the prevailing cell size in normal and infertile sample. Increased number of spots (each spot is one cell) in the upper right corner of the histogram of patient's sample (arrows, center) is indicative of a large number of morphologically abnormal, large spermatozoa, including those with superfluous cytoplasm. Epifluorescence microscopy was used to visualize Sptrx-3 (FIG. 8B, FIG. 8C) and ubiquitin (FIG. 8D, FIG. 8E) in sperm samples of a fertile donor (FIG. 8B, FIG. 8D) and a teratospermic patient (FIG. 8C, FIG. 8E; same subjects as shown in FIG. 8A). Corresponding differential interference contrast (DIC) images are shown in panels FIG. 8B, FIG. 8C, FIG. 8D, and FIG. 8E.

FIGS. 9A-F: Two dimensional (2-D) western blots of rat sperm proteins stained with anti-SPTRX-3 serum or post vasectomy rat sera. The arrows and arrowheads denote comparable points in each of the three blots. FIG. 9A, Antiserum raised against SPTRX-3 peptides bound two main constellations of proteins, at 24-29 kDa, pI 4.7-7.2, and 17-22 kDa, pI 5.8-7.5. The post vasectomy serum shown in panel C bound trains of protein spots at 24-29 and 17-22 kDa that migrated in a very similar pattern to that for SPTRX-3 (FIG. 9A). The second post vasectomy serum (FIG. 9E) showed a different pattern; although it did not react with the entire constellation of protein spots, it did stain spots that co-migrated with those at the acidic end of the 20-25 kDa train (short arrow) and at the basic end of the 17-22 kDa train (arrowhead). Blots stained with the corresponding pre-immune or pre-vasectomy sera (FIG. 9B, FIG. 9D, and FIG. 9F) showed no reaction or very faint staining; although two spots at 17-18 kDa, pI~7.0-7.3, were lightly stained in panel F, their staining with the corresponding post vasectomy serum was much increased (FIG. 9E).

DESCRIPTION OF ILLUSTRATIVE EMBODIMENTS

Figure 2:
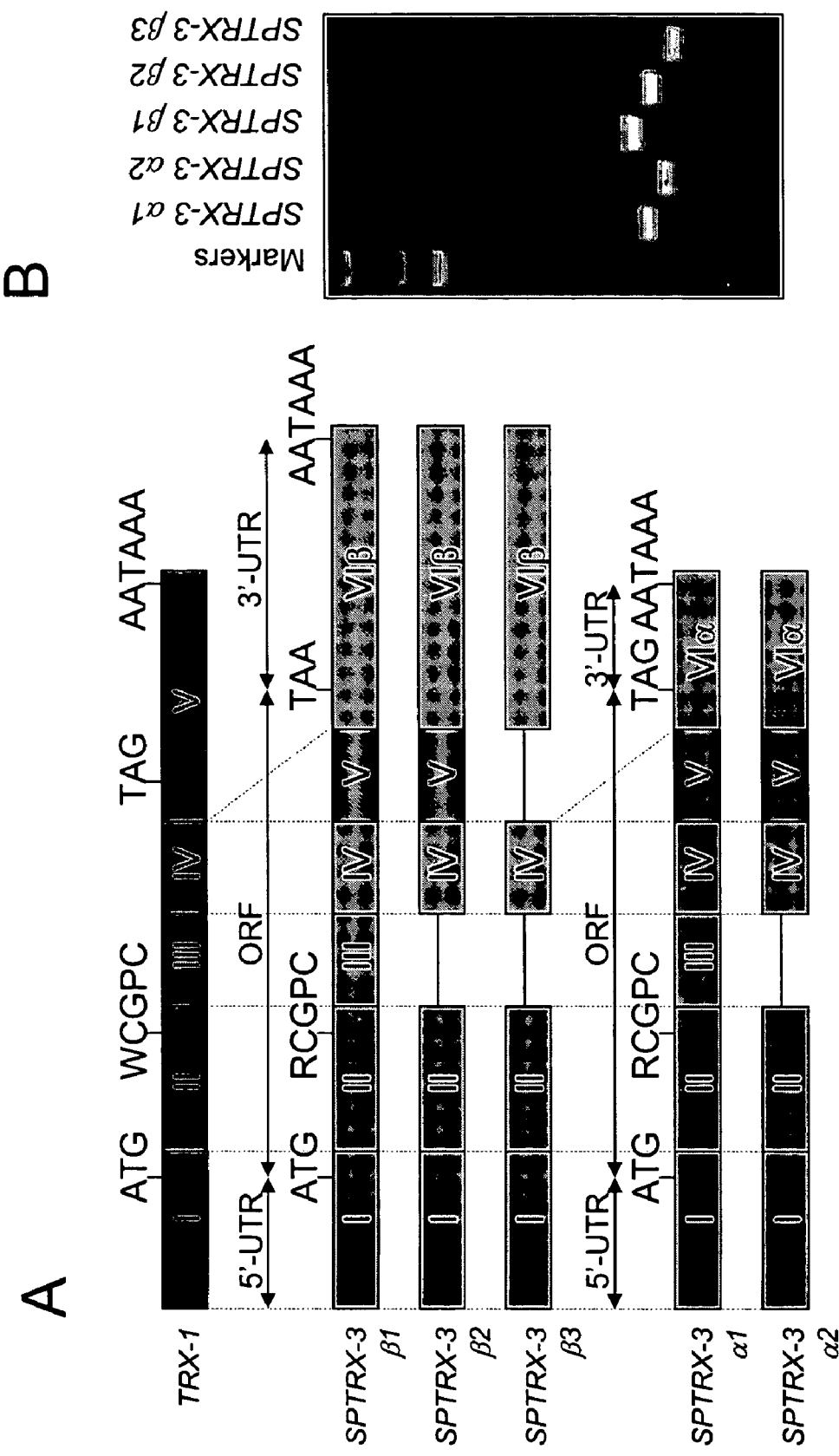
FIGS. 2A-B: Human Sptrx-3 isoforms.

The invention overcomes the limitations of the prior art by providing novel methods and compositions for the detection of infertility. As described above, there is a need for improved methods of evaluating fertility and diagnosing infertility. The invention therefore provides methods of ascertaining fertility of a sample of spermatozoa, as well as a subject, by detecting the presence and/or activity of the novel fertility marker Sptrx-3, or in the cases of autoimmune infertility, the presence of anti-Sptrx3 antibodies in subject's blood serum. The inventors have demonstrated that an elevation of Sptrx-3 presence and/or activity in association with a sample of spermatozoa is correlated with decreased fertility. Such levels may be evaluated as "elevated" or "increased" by comparison to control samples to establish and average or baseline for the population of subjects. A greater presence of Sptrx-3 relative to an average subject within a population, including a concentration that is in at least about the $60^{th}$, $70^{th}$, $80^{th}$, $90^{th}$, $95^{th}$ and $99^{th}$ percentile of concentration relative to fertile male subjects in the species being examined may be used to assess fertility. Similarly, the inventors have demonstrated the presence of anti-Sptrx3 antibodies in sera of vasectomized rats, an established model for inducing autoimmune infertility due to self-production of anti-sperm antibodies.

In accordance with the results of such aspects, various interventions for treatment of infertility may be taken, as is known in the art. In the case of livestock and animal breeding programs, male animals may be selected for entry into the breeding program based on such evaluations. Individual semen samples may also be evaluated for use in artificial insemination or in vitro fertilization and the like based on assays in accordance with the invention. Finally, human and animal sperm samples may be evaluated for their sperm-SPTRX3 levels in toxicologic studies for the purpose of drug development and/or compound testing, environmental quality monitoring, and monitoring of toxic workplace exposure.

As the expression of Sptrx-3 in mammals is highly conserved, the invention may find use with a number of species. The current invention may therefore find use with potentially any mammal including, but not limited to, for example, beef and dairy cattle, pigs, horses, cats, dogs, rodents, primates and, in a preferred embodiment, humans. Sptrx-3 enzymes, the nucleic acid and amino acid sequences of which having been identified by the inventors, as well as anti-Sptrx3 antibodies, may be detected in accordance with the invention using standard methodology for the detection of proteins, antibodies, and nucleic acids.

I. Thioredoxins

The thioredoxin (Trx) family of proteins comprises a group of proteins sharing a highly conserved active site with the sequence Cys-Gly-Pro-Cys (CGPC) implicated in catalyzing redox reactions through the reversible oxidation of the cysteine residues in their active site from a dithiol to a disulphide form. Thioredoxins are maintained in their reduced active form by the selenoprotein thioredoxin reductase (TrxR) which transfers electrons from NADPH. Together, thioredoxins and their reductases constitute the so-called thioredoxin system (Arner and Holmgren, 2000). All organisms from lower prokaryotes to humans are equipped with distinct thioredoxin systems that participate in diverse cellular processes, including among others modulation of transcription factor-DNA binding activity, DNA synthesis, antioxidant defense, regulation of apoptosis or immune response. Moreover, abnormal expression of some thioredoxin and/or thioredoxin reductase genes has been correlated with a number of pathologies such as cancer, Alzheimer's and Parkinson's diseases, AIDS, etc. (Gromer et al., 2004; Hirota et al., 2002; Holmgren, 2000; Powis and Montfort, 2001). Most, if not all of the functions assigned to thioredoxin are dependent on their ability to behave as general protein disulfide reductases.

Eukaryotic organisms have two complete thioredoxin systems, one in cytoplasm and the other in mitochondria (Hirota et al., 2002). Furthermore, a large number of different thioredoxins with novel properties such as organelle specific localization in endoplasmic reticulum or mitochondria (Cunnea et al., 2003; Hosoda et al., 2003; Miranda-Vizuete et al., 2000), tissue-specific distribution, and the microtubule-binding properties (Sadek et al., 2003), have recently been reported in mammals. This complexity is paralleled by the increasing number of thioredoxin reductase variants.

Based on protein domain organization, thioredoxins can be separated into two different groups: Group I encompasses those proteins consisting of one thioredoxin domain, while Group II includes those comprising thioredoxin domains plus additional non-thioredoxin domains. In humans, members of Group I are TRX-1 (Wollman et al., 1988) and TRX-2 (Spyrou et al., 1997) while Group II includes thioredoxin-like 1 (TXL-1), a thioredoxin-related protein of 32 kDa (TRP32) (Lee et al., 1998; Miranda-Vizuete et al., 1998), endoplasmic reticulum dj5 (ERdj5)/J-domain-containing protein disulfide isomerase-like protein (JPDI) (Cunnea et al., 2003; Hosoda et al., 2003), the spermatid-specific thioredoxin-1 (SPTRX-1) (Jimenez et al., 2002; Miranda-Vizuete et al., 2001), SPTRX-2 (Miranda-Vizuete et al., 2003; Sadek et al., 2001), and TXL-2 (Sadek et al., 2003).

Thus, an alternative classification of thioredoxins, based on the above expression patterns, can be proposed wherein all the ubiquitously expressed thioredoxins (TRX-1, TRX-2, TXL-1, ERDJ5) can be sorted out in one group, although some of them can be found in different subcellular compartments. The other group would then incorporate all those thioredoxins with a tissue specific expression such as SPTRX-1, SPTRX-2 and TXL-2, the first two specifically expressed in male germ cells and the third one in tissues harboring cilia and flagella such as spermatozoa or lung airway epithelia featuring microtubule-based motile structures. The abundance of tissue-specific thioredoxins in male germ cells reflects a key role of this family of proteins in spermatogenesis, further supported by the recent finding of a novel testis-specific splicing variant of cytosolic thioredoxin reductase and the Trx and GSSG reductase (TGR), a fusion protein of glutaredoxin and thioredoxin reductase domains with high expression in testis (Sun et al., 2001).

The major role of the fertilizing spermatozoon is to contribute the male pronucleus for the zygote. For this purpose, the round spermatid undergoes a dramatic morphological and biochemical adaptation that results in the highly polarized spermatozoon, in a process known as spermiogenesis (Oko, 1998). Morphologically, mature spermatozoon is composed of a head and a tail, and both structures are equipped with unique accessory structures, that are necessary for the spermatozoon to fulfill its function. Thus, apart from the nucleus where DNA is linked to protamines to facilitate a high condensation and stability, the sperm head contains the acrosome, an enzyme-filled membrane-enclosed vesicle that is required for the sperm-egg binding and the penetration of egg vestments during fertilization (Eddy and O'Brien, 1994). The sperm tail is responsible of energy production and mobility of the sperm cell which is achieved by the acquisition of additional cytoskeletal structures, namely the outer dense fibers and fibrous sheath, surrounding the sperm axoneme (Curry and Watson, 1995; Eddy and O'Brien, 1994).

The association of thioredoxin proteins to the male germ cell lineage appears to be a key event in spermatogenesis. In addition to mammals, it is also found in lower eukaryotes, such as sea urchin (Ogawa et al., 1996) or *Drosophila melanogaster* (Svensson et al., 2003).

The present invention discloses the characterization of a novel thioredoxin, named Sptrx-3, exclusively expressed in testis and possibly required for the biogenesis of the acrosome. Additionally, Sptrx-3 expression is altered in several pathologies associated with male reproductive physiology. Thus, Sptrx-3 arises as a specific marker for defective spermatozoa from infertile males as well as a novel sperm post-obstruction autoantigen.

II. Diagnostic Assays

In accordance with one aspect of the invention, methods are provided for assaying fertility by detecting for the presence of a Sptrx-3 enzyme and/or activity thereof in association with spermatozoa samples. As is known to those of skill in the art, the detection of the presence of a given enzyme such as Sptrx-3 need not be carried out on the enzyme itself, and may be carried out, for example, on one or more product catalyzed by the enzyme. Thus when detection of Sptrx-3 is referred to herein, this includes indirect detection of precursors and/or products of Sptrx-3, and the detection of anti-Sptrx3 antibodies a in subjects' blood sera. Examples of such compounds that may be detected to show the presence of Sptrx-3 include products which are catalyzed by Sptrx-3. Sptrx-3 substrates may include: 5,5'-dithiobis(2-nitrobenzoic acid) (DTNB), 5-thiobis(2-nitrobenzoic acid) (TNB), GSSG (oxidized glutathione), lipoic acid, protein disulfides, alloxan, vitamin k, NK-lysin, L-cystine, protein disulfide isomerase, and peroxiredoxins. Certain assays for determining thioredoxin activity are well known in the art (e.g., Holmgren, A, 1984) and may be used with the present invention to determine Sptrx-3 activity.

Many assay formats for detecting the presence and/or activity of enzymes are well known to those of skill in the art and may be used in accordance with the invention for detection of Sptrx-3. Such assays may be qualitative or quantitative. Examples of some of these are described below for illustrative purposes.

A. Immunologic Detection of Sptrx-3

One aspect of the present invention entails the use of antibodies in the immunologic detection of Sptrx-3. Various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), Western blotting, and radioimmunoassays (RIA). Immunohistochemical detection using tissue sections and immunocytochemical detection using isolated cells also is particularly useful. However, it will be readily appreciated that detection is not limited to such techniques, and one and two-dimensional PAGE, Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Such a sample will generally contain spermatozoa of a subject being analyzed, for example, semen.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with Sptrx-3. After this time, the Sptrx-3-antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the Sptrx-3 or the Sptrx-3-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the Sptrx-3 or anti-Sptrx-3 antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

B. ELISA

As a part of the practice of the present invention, the principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Makler et al., 1981; Samgadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In one embodiment, the invention provides a "sandwich" ELISA, where anti-Sptrx-3 antibodies are immobilized onto a selected surface, such as a well in a polystyrene microtiter plate or a dipstick. Then, a test composition suspected of containing Sptrx-3, e.g., a clinical sample, is contacted with the surface. After binding and washing to remove non-specifically bound immunocomplexes, the bound antigen may be detected by a second antibody to the Sptrx-3. In addition to antibodies raised against purified or recombinant Sptrx3, sera from subjects with autoimmune infertility could be used as the primary anti-Sptrx3 antibody in such assay, to diagnose subjects with anti-sperm antibodies.

In another exemplary ELISA, polypeptides from the sample are immobilized onto a surface and then contacted with the anti-Sptrx-3 antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the Sptrx-3 antibodies are immobilized involves the use of antibody competition in the detection. In this ELISA, labeled antibodies are added to the wells, allowed to bind to the Sptrx-3, and detected by means of their label. The amount of Sptrx-3 in a sample is determined by mixing the sample with the labeled antibodies before or during incubation with coated wells. The presence of Sptrx-3 in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

To provide a detecting means, the second or third antibody will have an associated label to allow detection. Commonly, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunocomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analytes.

C. Immunohistochemistry

While primarily useful in research contexts, immunohistochemistry may be useful according to the present invention in identifying Sptrx-3. This involves testing of both fresh-frozen and formalin-fixed, paraffin-embedded tissue blocks prepared from study by immunohistochemistry (IHC). For example, each tissue block consists of 50 mg of residual "pulverized" placental tissue. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" placental tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 remarkably intact placental cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

D. Immunodetection Kits

In further embodiments, the invention provides immunological kits for use in detecting Sptrx-3 in biological samples. Such kits will generally comprise one or more Sptrx-3 or Sptrx-3-binding proteins that have immunospecificity for various Sptrx-3 and for antibodies. More specifically, the immunodetection kits will thus comprise, in suitable container means, one or more antibodies that bind to Sptrx-3, and antibodies that bind to other antibodies via Fc portions.

In certain embodiments, the Sptrx-3 or primary anti-Sptrx-3 antibody may be provided bound to a solid support, such as a column matrix or well of a microtitre plate. Alternatively, the support may be provided as a separate element of the kit.

The immunodetection reagents of the kit may include detectable labels that are associated with, or linked to, the given antibody or Sptrx-3 itself. Detectable labels that are associated with or attached to a secondary binding ligand are also contemplated. Such detectable labels include chemiluminescent or fluorescent molecules (rhodamine, fluorescein, green fluorescent protein, luciferase), radioabels ($^3H$, $^{31}S$, $^{32}P$, $^{14}C$, $^{131}I$) or enzymes (alkaline phosphatase, horseradish peroxidase).

The kits may further comprise suitable standards of predetermined amounts, including both antibodies and Sptrx-3. These may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, Sptrx-3 and any other reagent containers in close confinement for commercial sale. Such containers may include injection or blow-molded plastic containers into which the desired vials are retained.

III. Generating Antibodies Reactive With Sptrx-3

In another aspect, the present invention contemplates an antibody that binds immunologically with a Sptrx-3 molecule, or any portion thereof. An antibody can be a polyclonal or a monoclonal antibody composition. Means for preparing and characterizing antibodies are well known in the art (see, e.g., Harlow and Lane, 1988).

A polyclonal antibody is generally prepared by immunizing an animal with an immunogen comprising a peptide or polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of Sptrx-3 can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

Monoclonal antibodies may find use with the invention in standard immunochemical procedures, such as ELISA and Western blot methods and in immunohistochemical procedures such as tissue staining, as well as in other procedures which may utilize antibodies specific to Sptrx-3-related antigen epitopes. Additionally, it is proposed that monoclonal antibodies specific to the particular Sptrx-3 of different species may be utilized in other useful applications.

In general, both polyclonal and monoclonal antibodies against Sptrx-3 may be used in a variety of embodiments. For example, they may be employed in diagnostic as well as therapeutic applications. They may also be used in inhibition studies to analyze the effects of Sptrx-3 related peptides in cells or animals. Anti-Sptrx-3 antibodies will also be useful in immunolocalization studies to analyze the distribution of Sptrx-3 polypeptides, for example, during maturation o spermatozoa. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Sptrx-3. The immunizing composition is administered in a manner effective to stimulate antibody producing cells. Rodents such as mice and rats are preferred animals; however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes.

Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Purification and Detection of Sptrx-3 or Activity Thereof

In certain aspects of the invention, techniques may be used for the isolation or removal of Sptrx-3 or antigens thereof from a sample. For example, Sptrx-3 may be isolated for further use as well as for generation of one or more diagnostic reagents. One or more purification techniques may also find use in accordance with the invention for the improvement of semen sample quality by way of reduction of Sptrx-3 content.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification of a protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of Sptrx-3, or assessing the amount of Sptrx-3 polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number" (i.e., 2-fold, 5-fold, 10-fold, 50-fold, 100-fold, 1000-fold, etc.). The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE and according to how extensively it is glycosylated (Capaldi et al, 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of min, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

In some embodiments of the present invention, it may be desirable to use recombinant expression to express Sptrx-3. Multiple systems for recombinant expression are well known in the art. Preferred non-limiting embodiments of systems for recombinant expression include the use of expression in bacterial, yeast, insect, and/or mammalian cell systems. Nonlimiting examples of bacterial systems that can be used for recombinant expression include histag, GST-fusion, and MBP systems (e.g., Uchiki et al., 2002; Zhan et al., Routzhan et al., 2002). Nonlimiting examples of yeast systems that can be used for recombinant expression include the *Pichia pastoris* system (e.g., Invemizzi et al., 2004). Other U.S. patents which provide examples of recombinant expression systems include U.S. Pat. Nos. 6,558,924, 6,521,424, 6,194,176, 5,876,969, and 5,670,360.

V. Detection of Nucleic Acids Encoding Sptrx-3

In addition to their use in directing the expression of Sptrx-3 protein (SEQ ID NO:10), polypeptides and/or peptides, the nucleic acid sequences disclosed herein have a variety of other uses. For example, they have utility as probes or primers for embodiments involving nucleic acid hybridization.

A. Hybridization

In certain embodiments of the present invention, probes or primers may be used to hybridize with nucleotides encoding Sptrx-3 (SEQ ID NO:9). The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such "high stringency conditions" tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:9 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

E. Kits for Detecting Sptrx-3

All the essential materials and/or reagents required for detecting SEQ ID NO:9 in a sample may be assembled together in a kit. This generally will comprise a probe or primers designed to hybridize specifically to individual nucleic acids of interest in the practice of the present invention, including SEQ ID NO:9. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods cDNA Cloning of Human, Mouse and Rat Sptrx-3 Genes: The Basic Local Alignment Search Tool (BLAST) (Altschul and Koonin, 1998) was used to perform a survey of different databases at the National Center for Biotechnology Information (www.ncbi.nlm.nih.gov) to identify new entries encoding potential novel members of the thioredoxin family. Using the sequence of human TRX-1 as bait, the inventors found one sequence supported by the expressed sequence tag (EST) entry AI188241 to encode a novel human putative thioredoxin-like protein. Based on this sequence, the nested forward primers F1 (5'-GAGGCCTGGTGTAATCATGGTA-CAG-3'; SEQ ID NO:1) and F2 (5'-CAACAGGGGATTTTCATCAGCACTTC-3'; SEQ ID NO:2) were used for 3'-rapid amplification of cDNA ends (RACE) on a human testis cDNA library (Clontech, Palo Alto, Calif., USA). Based on the sequence obtained, the nested forward primers R1 (5'-CGAGTTTGTGTCCG-GCAGCTGTC-3'; SEQ ID NO:3) and R2 (5'-CTGTACCAT-GATTACACCAGGCCTC-3'; SEQ ID NO:4) were used for 5'-RACE in the same library. The resulting sequences were used to amplify by PCR the full-length α and β forms as well as Δ3Sptrx-3p, Δ3-5Sptrx-3β and Δ3Sptrx-3α cDNA of human Sptrx-3 from the same library. The amplification products were cloned in the pGEM-Teasy vector (Promega, Madison, Wis., USA) and sequenced in both directions.

For the mouse and rat orthologues, the same strategy was followed using human Sptrx-3 sequence and blasted against the mouse and rat EST databases (www.ncbi.nlm.nih.gov). By these means several mouse and rat sequences were obtained (Mouse EST BY714796 and Rat EST A1764117.1) and used to design specific primers at the putative translation initiation and stop codons and to amplify by PCR the mouse and rat Sptrx-3 open reading frames (ORFs) from a mouse or rat testis cDNA library respectively (Clontech).

Northern Blot Analysis: Human Multiple Tissue Northern (MTN) blots and human Multiple Tissue Expression (MTE) arrays with poly(A)+ RNA from different tissues were purchased from Clontech. The human Sptrx-3 ORF was labeled with [α-$^{32}$P] dCTP (Rediprime random primer labeling kit; Amersham Pharmacia-Biotech, Uppsala, Sweden) and hybridized at 65° C. overnight in ExpressHyb Solution following the protocol provided by Clontech. The blots were also hybridized with human β-Actin ORFas control. The blots were scanned and quantified with the Gel Pro Analyzer program (Media Cybernetics, Silver Spring, Md., USA).

Antibody Production: Peptide sequences for immunizing rabbits were derived from the human Sptrx-3 protein sequence to raise specific antibodies against human Sptrx-3, but with the ability to cross-react with mouse and rat Sptrx-3. With that aim two different peptides named exon I: ($NH_2$—)MVQIIKDTNEFKTFC (—COOH) (SEQ ID NO:5) and exon Tse: (Ac-)VTLFSRIKRIIC (—COOH) (SEQ ID NO:6) were synthesized and used to immunize rabbits (Agrisera, Vannas, Sweden). After four immunizations serum was collected and polyclonal antibodies were purified by affinity chromatography using 4 mg of an exon I/exon V peptide mix conjugated to UltraLink matrix from Pierce (Rockford, Ill., USA). Specificity of the antibodies was confirmed by ELISA against the peptides and by western-blot analysis.

Enzymatic Activity Assays: Two different enzymatic assays were used to determine the capability of human Sptrx-3 to reduce insulin in vitro in crude cellular extracts. In the so-called DTT assay, DTT (dithiothreitol; Sigma) was used as reducing agent, and the assay was carried out as previously described (Wollman et al., 1988). The second assay used thioredoxin reductase and NADPH (Sigma-Aldrich, St. Louis, Mo., USA) as electron donors for thioredoxin and was performed essentially as described elsewhere (Spyrou et al., 1997). In both cases, human Trx1 was used as control.

Preparation of Spermatozoa and Extraction of Sperm Proteins: Human Semen samples were collected from healthy donors who signed appropriate consent forms. Samples were allowed to liquefy at room temperature and were separated from seminal plasma by centrifugation (1000×g) for 10 min at room temperature. After two washes in PBS, the pelleted spermatozoa were frozen at −20° C. until use. The sperm pellet was solubilized in a lysis buffer containing 0.1 M Tris-HCl, pH 8.0, 0.15 M NaCl, protease inhibitor mixture (Roche Molecular Biochemicals), and phosphatase inhibitor mixture (Sigma-Aldrich) at the concentration recommended by the manufacturers. Samples were then subjected to three cycles of freezing/thawing in dry ice/ethanol, incubated for 30 min on ice, and centrifuged at 14,000 rpm for 30 min. The soluble fraction was used for further analysis.

In Situ Hybridization: Human testes were obtained with patients' informed consent from orchiectomies performed due to prostate cancers. In situ hybridization was carried out as described previously (Kononen and Pelto-Hiukko, 1997 (tto.trends.com)). The samples were frozen on dry ice, sectioned with a Microm HM 500 cryostat at 14 μm, and thaw-mounted onto poly-L-lysine glass slides. The sections were stored at −20° C. until use. Four oligonucleotide probes (ATGGTACAGATTATTAAAGAC SEQ ID NO: 14, GACAGCTGCCGGACACAAACTCG SEQ ID NO: 15, GTGGATGTGAACAATTCTCCGG SEQ ID NO:16, GAAGTGGATTCATGAGCAACCTG SEQ ID NO:17 of human Sptrx-3 cDNA) were used. All probes produced similar results when used separately and were usually used simultaneously to intensify the signal.

Several control probes with the same length and similar GC content and specific activity were used to determine the specificity of the hybridization.

Immunohistochemistry: Paraffin sections containing multiple human tissues (T1065; lot 9994A) were purchased from Dako (Copenhagen, Denmark). In addition, paraffin sections of human testis were used. Immunohistochemistry was performed as described previously (Rybnikova et al., 2000) either by the ABC method or by the indirect immunofluorescence method using goat anti-rabbit fluorescein isothiocyanate (1:100, 30 min; Roche Molecular Biochemicals) as a secondary antibody. The processed tissue sections were embedded in PBS-glycerol mixture containing 0.1% p-phenylenediamine. The sections were examined with a Nikon Microphot-FXA microscope equipped with proper fluorescent filters.

Immunoelectron Microscopy: Procedures for electron microscopy immunocytochemistry were described previously (Oko, 1998; Shao et al., 1997). Affinity-purified anti-Sptrx-3 antibodies were used at a 1:20 dilution, and colloidal gold-conjugated goat anti-rabbit IgG at a 1:20 dilution was the secondary antibody.

Green Fluorescent Protein Analysis: The pBI-EGFP vector (Clontech) was used to express human Sptrx-3 and GFP proteins bidirectionally. The following mutagenic primers were used: 5'-GAGGACGCGTGCCACCATGGTACAGAT-TATTAAAG-3' (SEQ ID NO:7) as forward primer and 5'-CT-TGGCTAGCTTATTACATTAATTCTTGAG-3' (SEQ ID NO:8) as reverse primer to amplify human Sptrx-3 from pGEM-Te/Sptrx-3. The forward primer introduces an MluI site followed by a Kozac sequence (Kozak 1996) and the reverse primer introduces a NheI site. The amplified DNA was cloned into the MluI-NheI sites of pBI-EGFP expression vector and E. coli TOP-10 F' strain was transformed with the recombinant plasmid pBI-EGFP/Sptrx-3. The plasmid was purified using the midi-prep kit (Qiagen, Chatsworth, Calif., USA) and sequenced. An identical strategy was used with TRX-1 in order to use it as a control in all of experiments.

Transfection studies were performed with 1 mg of DNA diluted in 10 ml of $H_2O$ and 0.5 ml of 0.1M PEI (polyethylenimine, Sigma-Aldrich). The mixture was mixed thoroughly, incubated at room temperature for 10 min and subsequently added to the medium and applied on to HEK293 cells. The GFP images were acquired with a Leica laser scanning confocal microscope using the 488 nm line of an ArKr laser, and emitted light was collected at the 500-540 nm wavelength range. 7-AAD was excited with the 568 nm line and emitted light was collected at 640-680 nm wavelength.

Sperm Samples from Infertile Men: Infertile, teratospermic samples originated from patients diagnosed with male factor infertility at the infertility clinic of CEGyR, Buenos Aires Argentina. All 19 patients were clear cases of severe male infertility with abnormally low sperm counts and sperm motility by WHO criteria and abnormally low % normal sperm morphology by Krueger's strict criteria. All 19 patients and their spouses underwent IVF or ICSI treatment, with only two couples achieving pregnancies, neither of which was carried to term. Control samples from 5 fertile donors with excellent sperm count motility and morphology by WHO criteria were purchased from Fairfax Cryobank, Fairfax, Wash., USA. All sperm samples were collected from informed, consenting donors and handled in accordance with the protocols approved by Internal Review Boards of the University of Missouri-Columbia and CEGyR, Buenos Aires, Argentina.

Flow Cytometry and Epifluorescence Microscopy: Procedures were described in detail by Sutovsky et al., (2001). Briefly, sperm samples were thawed, washed by centrifugation through TL-Hepes medium and fixed for 40 minutes in 2% formaldehyde. Sperm suspensions were permeabilized with 0.1% Triton X-100 and blocked in 5% normal goat serum (NGS), collected by centrifugation and split into two equal sperm pellets. One pellet from each donor was incubated for 40 min with the anti-Sptrx-3 serum (described above; dil. 1/100), followed by goat anti-rabbit-FITC (Zymed Labs, S. San Francisco, Calif.; dil. 1/80). The other half was incubated with monoclonal antibody KM 691 (Kamiya Biomedical Company, Seattle, Wash.; dil. 1/100) against recombinant human ubiquitin, an established sperm abnormality marker (Sutovsky et al., 2001; Rawe et al., 2002), and detected with FITC-conjugated goat anti-mouse IgM (Zymed; dil. 1/80). Blank, negative control samples were prepared by omitting the primary antibody.

Flow cytometry was performed using FACS Scan Analyzer (Becton Dickinson), set at 488 nm wavelength. Relative levels of Sptrx-3- or ubiquitin-induced fluorescence in 10,000 individual cells/sample were recorded. Scatter diagrams visible light and histograms of antibody-induced fluorescence were generated for each sample. The median values of antibody-induced fluorescence (Sptrx-3-medians or Ubi-medians) were compared between infertility patients and fertile donors using statistical tools (ANOVA and Person's correlation) in MS Excel and SAS version 8.2. Each sample was also screened by epifluorescence microscopy. Ten microliters of each sperm pellet processed for flow cytometry were mounted under a coverslip on a conventional microcopy slide and photographed using Nikon Eclipse 800 microscope with high numerical aperture objectives, and a Cool Snap HQ CCD camera (Roper Scientific, Tucson, Ariz.), operated by MetaMorph imaging software (Universal Imaging Corp., Downington, Pa.). Images were archived on recordable CDs and printed on an Epson Stylus Photo 1280 printer using Adobe Photoshop 6.0 software (Adobe Systems, Mountain View, Calif.).

Western Blot Analysis of Sperm Autoantibodies: Adult male Lewis rats (225-275 g), purchased from Charles River Laboratories (Wilmington, Mass., USA), received bilateral vasectomy as previously described (Flickinger et al., 1999). Sera were collected prior to vasectomy and 3 months after the surgery. All procedures were conducted with the approval of the Animal Research Committee of the University of Virginia-School of Medicine and in accordance with the Guide for the Care and Use of Laboratory Animals and other relevant publications.

Sperm samples were isolated from the cauda epididymidis of Lewis rats by back-flushing fluid through the vas deferens (Flickinger et al., 1999). One (1-D) and two-dimensional (2-D) gel electrophoresis and western-blot was performed as described previously (Miranda-Vizuete et al., 2003)

Figure 1:
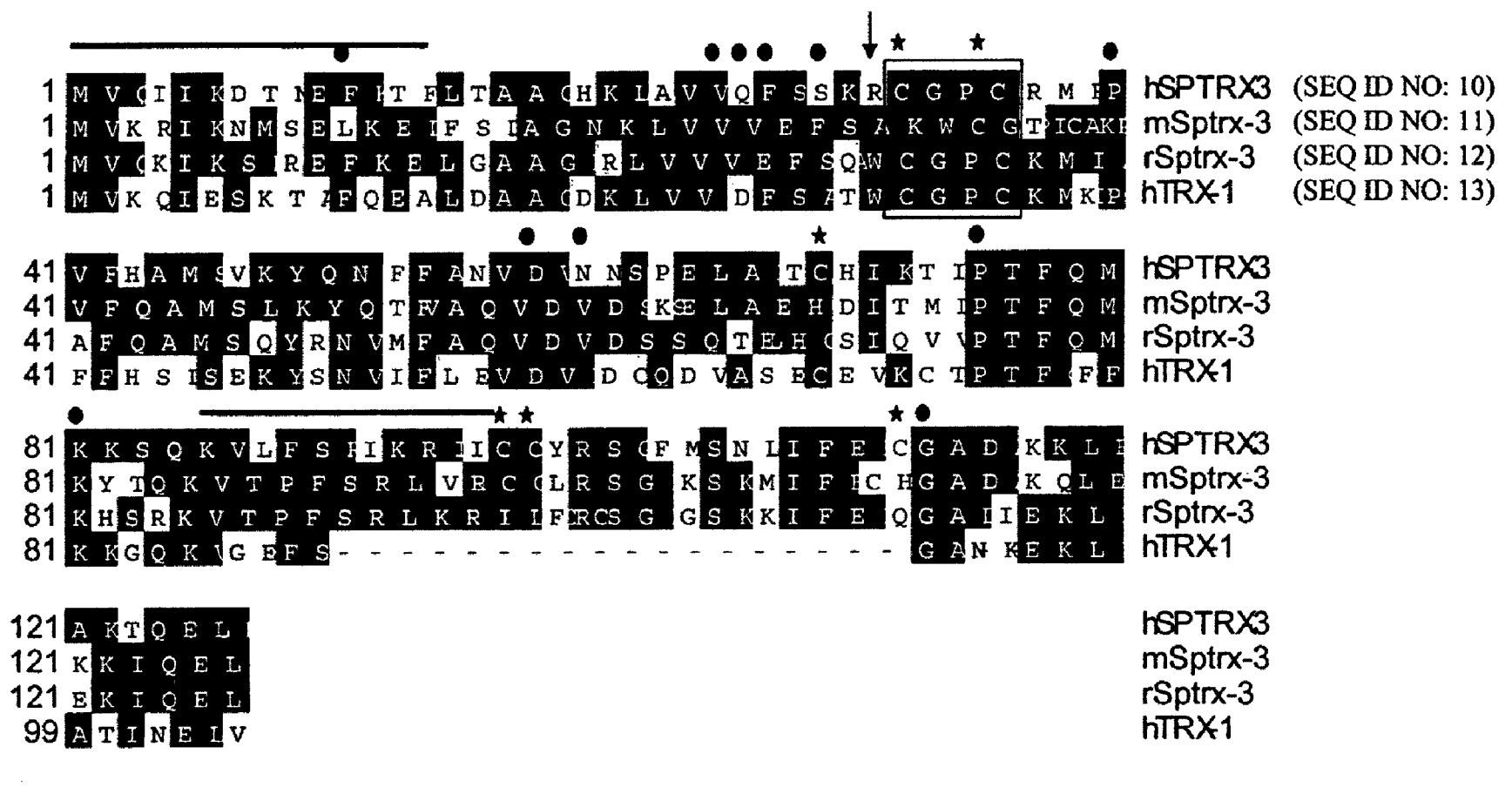

Example 2 cDNA Cloning, Sequence Analysis, Genomic Organization and Chromosomal Localization of Human, Mouse and Rat Sptrx-3 Gene By sequence comparison with human TRX-1 gene, the inventors found that GenBank expressed sequence tag AI188241 (from human testis) encoded a putative novel thioredoxin sequence containing the matching CGPC thioredoxin consensus motif. Based on this sequence primers were designed to perform 5' and 3'-RACE analysis using a human testis cDNA library to clone the full-length cDNA of this novel protein. The complete cDNA sequence consists of a 384 bp ORF, a 97 bp 5'-UTR and a 376 bp 3'-UTR with one canonical poly-$(A)^+$ sequence (Human Sptrx-3 DNA SEQUENCE; SEQ ID NO:9). The inventors also cloned the rat and mouse orthologues of human Sptrx-3 cDNA aided by homology searches using the human ORF as bait (www.ncbi.nlm.nih.gov/BLAST/). Both mouse and rat Sptrx-3 ORFs encode a protein highly similar to that of human Sptrx-3 (FIG. 1).

Human 3'-RACE analysis rendered four additional products, which were also cloned. Two of them corresponded to different splicing variants of the full-length cDNA described above while the other two arose from alternative splicing of the last exon which translation would result in a shorter protein differing at its C-terminus (FIG. 2).

A sequence comparison in the Human Genome Sequence Data Base (www.ncbi.nlm.nih.gov/genome/guide/human/) mapped the Sptrx-3 genomic region at human chromosome 9q32 (entry NT-008470) just downstream to TRX-1 gene, between the markers D9S1828 and D9S1835 (based on the deCODE-high resolution recombination map of human genome; (Kong et al., 2002)). Using the Genomatix Software (www.genomatix.de/) the inventors determined that human Sptrx-3 gene spans 35 kb and is organized into six exons and five introns, all according to the GT/AG rule. Similar to the human Sptrx-3 gene, the mouse and rat genomic regions were determined to be located at chromosomes 4B3 and 5q22, both syntenic to that of the human gene and also organized into 6 exons and five introns.

Intriguingly, Sptrx-3 genomic organization is identical to that of TRX-1 (including exon-intron splicing sites) except for Sptrx-3 exon V and such resemblance strongly suggests a genomic duplication event as the explanation for Sptrx-3 origination. This is confirmed by a phylogenetic analysis of all human thioredoxin proteins that place TRX-1 and Sptrx-3 in the same, independent branch. As previously mentioned, two different forms of the last exon can be found within Sptrx-3 sequence, designed VIβ for the shorter and VIβ for the longer exon, respectively (FIG. 2). Interestingly, exon VIα is located immediately upstream of exon VIβ within the genomic sequence, in a similar fashion to that described for glutaredoxin-1 (GRX-1), a related member of the thioredoxin family (Spyrou et al., 2001). The remaining variants of Sptrx-3 originate from splicing of exon III alone or together with exon V (see FIG. 2 for nomenclature of these variants). The inventors chose the Sptrx-3 β1 form for further work because the vast majority of EST entries in the human, mouse and rat databases correspond to this isoform (which is subsequently referred to as Sptrx-3).

Human Sptrx-3 ORF encodes for a protein of 127 amino acids (FIG. 1), which corresponds to a unique thioredoxin domain, with an estimated molecular weight of 14.6 kDa. A search for predicted sorting signal to specific subcellular locations at the PSORT II server (psort.nibb.ac jp/) failed to identify display any localization or retention signal in Sptrx-3 sequence.

Human, mouse and rat Sptrx-3 proteins show a high degree of homology (FIG. 1) and most of the amino acids known to be essential for catalysis, maintenance of three-dimensional structure, or protein-protein interactions in previously characterized thioredoxins (Eklund et al., 1991) are conserved in the three orthologues or replaced by others with similar properties. Interestingly, human Sptrx-3, but not murid Sptrx-3, is the first thioredoxin whose CGPC active site is preceded by an arginine residue instead of a tryptophan. The significance of this substitution remains unclear although it suggests specific properties for the human protein. With regard to structural cysteine residues (those not located at the active site), Sptrx-3 lacks Cys-62 and Cys-73, present in human TRX-1 while Cys-69 (all numbers referred to human TRX-1 residues) is conserved. Two additional cysteines at positions 97 and 98 are present in the three Sptrx-3 orthologues and one more cysteine exists at position 112 in human Sptrx-3. Interestingly, these three additional cysteines are located in exon V, the only one missing in human TRX-1 (FIG. 1).

Compared with other thioredoxins, the biochemical properties of human Sptrx-3, as well as mouse and rat Sptrx-3, differ substantially. Its isoelectric point is basic and the net charge is positive (9.47 and 10.23 respectively), contrasting with most previously described thioredoxins which have negative net charges and acidic isoelectric points.

Thioredoxins may regulate spermatogenesis by maintaining the appropriate redox environment for germ cell differentiation. Human Sptrx-3 and Trx-1 genes appear to have almost identical genomic organization, with the only difference of Sptrx-3 having an extra exon (exon V). Furthermore, both genes map at a narrow chromosomal region at 9q31-q32 and their protein sequence show approximately 50% identity. All these features strongly support the probable origin of Sptrx-3 as a genomic duplication of a Trx-1 gene ancestor. Through evolution, Sptrx-3 might have acquired some additional sequence corresponding to exon V (testis-specific) and, in turn, some additional function in spermatogenesis with the ancestor retaining its original function in a process called neofunctionalization (Lynch and Conery, 2000). This duplication event can be traced down at least before the hominid/rodent radiation as both genes can be found in mouse and rat.

Example 3

Sptrx-3 mRNA Expression is Restricted to the Male Germ-Line

Figure 3:
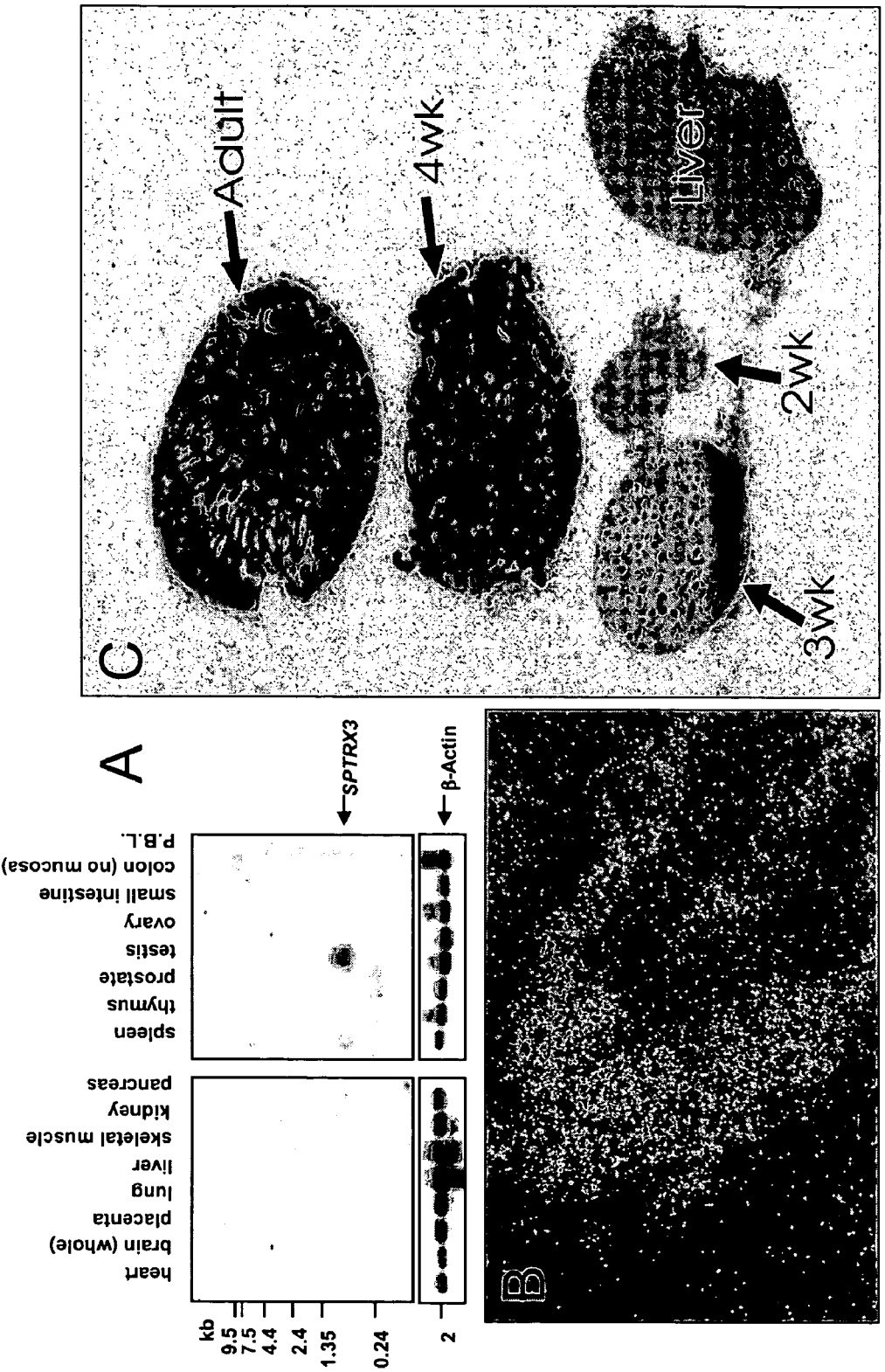
FIGS. 3A-C: Expression pattern of Sptrx-3 mRNA.

Multiple Tissue Northern (MTN; Clontech) blots were used to determine the size and tissue distribution of human Sptrx-3 mRNAs using the ORF as the probe. Human Sptrx-3 mRNA was detected after 48 hours of exposure only in human testis as a single band of ~0.9 kb in good agreement with the size of the cloned cDNA (FIG. 3A). No signal was obtained in any other tissue after longer exposure. To evaluate the possibility that Sptrx-3 mRNA could be expressed in other tissues not present in these blots, the inventors also screened a Multiple Tissue Expression (MTE; Clontech) Array containing poly(A)$^+$ RNAs from 50 different human tissues. Among the tissues examined, hybridization signal was observed only in testis mRNA. In situ hybridization on mouse testis demonstrated Sptrx-3 mRNA expression is restricted to spermatocytes and round spermatids, and no signal was detected in the other testicular cell types (FIG. 3B). Regarding the expression of Sptrx-3 mRNA during mouse testis development, results show that Sptrx-3 mRNA appears during the third week post-partum and increases in the fourth week and up to adult stage (FIG. 3C). These expression patterns are further shown in Jimenez et al. (2004).

Example 4

Cellular and Subcellular Expression of Sptrx-3 Protein in Testis

Figure 4:
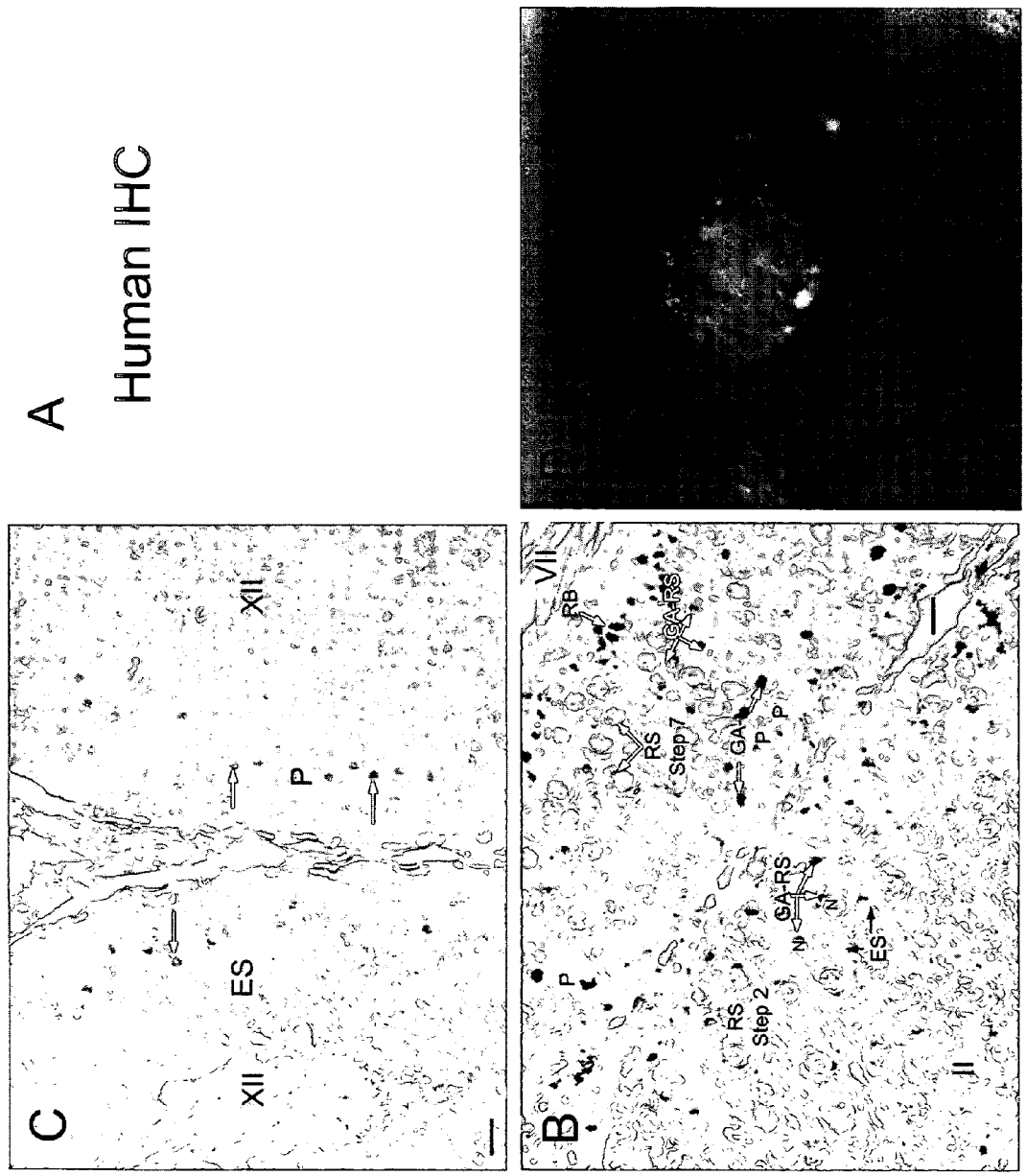
FIGS. 4A-D: Expression pattern of Sptrx-3 protein.

To address the expression pattern of Sptrx-3, affinity purified antibodies raised against two different peptides from human Sptrx-3 exon I and exon V were used (FIG. 1). Immunohistochemistry was first performed in human testicular sections, which revealed that Sptrx-3 expression was restricted to spermiogenesis and most prominently expressed in spermatocytes and round spermatids (FIG. 4A). However, the temporal sequence of expression was difficult to determine at the histological level because of the intermingling of stages within the human seminiferous tubules. Hence, the expression of Sptrx-3 was analyzed in detail in rat and mouse testicular sections, in which the stages of the seminiferous epithelium are clearly delineated. As shown in FIG. 4B and FIG. 4C, Sptrx-3 immunostaining was readily detected in close association to the Golgi of late spermatocytes and round spermatids in rat testicular sections. Such Sptrx-3 localization strongly suggests a role during acrosome biogenesis, as it is first identified in the Golgi located in a juxta-nuclear position in early round spermatids and later dissociated from the acrosome in the Golgi of late round spermatids (FIG. 4B and FIG. 4C). The Golgi of elongating spermatids does not appear to be labeled. Isolated mouse secondary spermatocytes also show labeling of the acrosomal granule (FIG. 4D). Rat testis showed a similar distribution pattern of Sptrx-3 labeling. No signal was detected in the presence of preimmune serum or immuno-absorbed antibody preparation using a mix of both peptides thus confirming the specificity of the antibodies and their immuno-reactivity in rodent samples.

Expression of Sptrx-3 was evaluated in human spermatozoa and in mouse spermatids and spermatozoa using immunohistochemistry. In human semen, Sptrx-3 is invariably found in the nuclear vacuoles and in the superfluous cytoplasm of morphologically abnormal spermatozoa. Similarly, mouse round spermatids express Sptrx-3 mainly in distinct cytoplasmic foci (probably Golgi), with increased expression in presumably apoptotic spermatids, expressing the pro-apoptotic cell surface protein Fas. Sptrx-3 expression in mature mouse spermatozoa is restricted to cytoplasmic droplets. Increased expression has not been observed in defective mouse spermatozoa.

Figure 5:
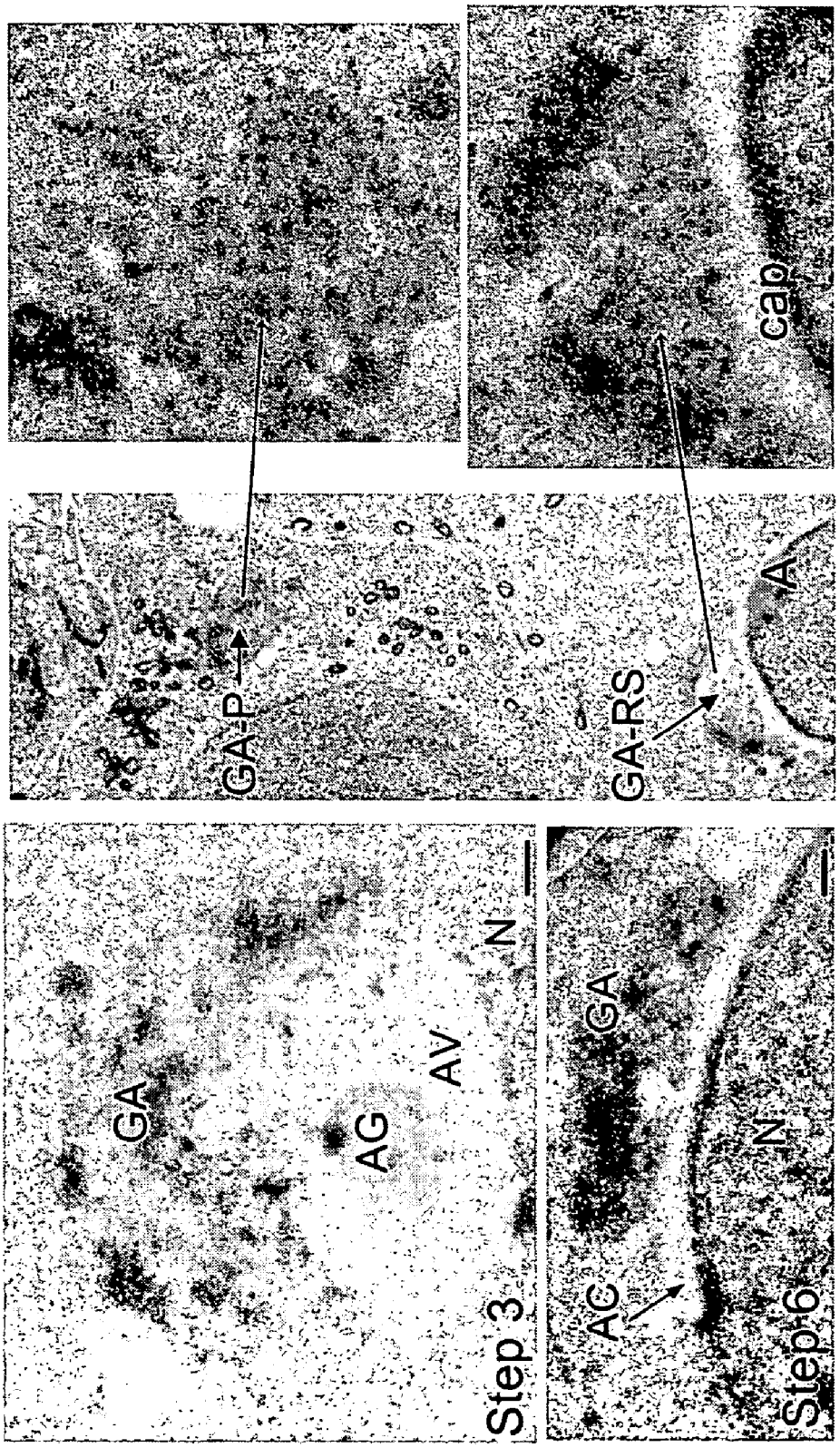
FIG. 5: Electron micrograph of a step 3 and 6 rat spermatid immunogold labeled with anti-Sptrx-3 antibody. Labeling is specific to the Golgi apparatus (GA) and forming acrosome of the round spermatid. AG, acrosomal granule; AV, acrosomal vesicle; AC, acrosomal cap; N, nucleus of spermatid. Bar, 0.2 μm. Note that the Golgi apparatus (GA) of the round spermatid (RS) and of the pachytene spermatocyte (P) specifically immunogold label with anti-Sptrx-3 antibody.

To confirm that Sptrx-3 might be involved in the acrosome biogenesis, immunogold electron microscopy was performed on rat samples, and a clear association of Sptrx-3 with the forming acrosome in pachytene spermatocytes and round spermatids was found, agreeing with previous light microscopy results (FIG. 5)

Figure 6:
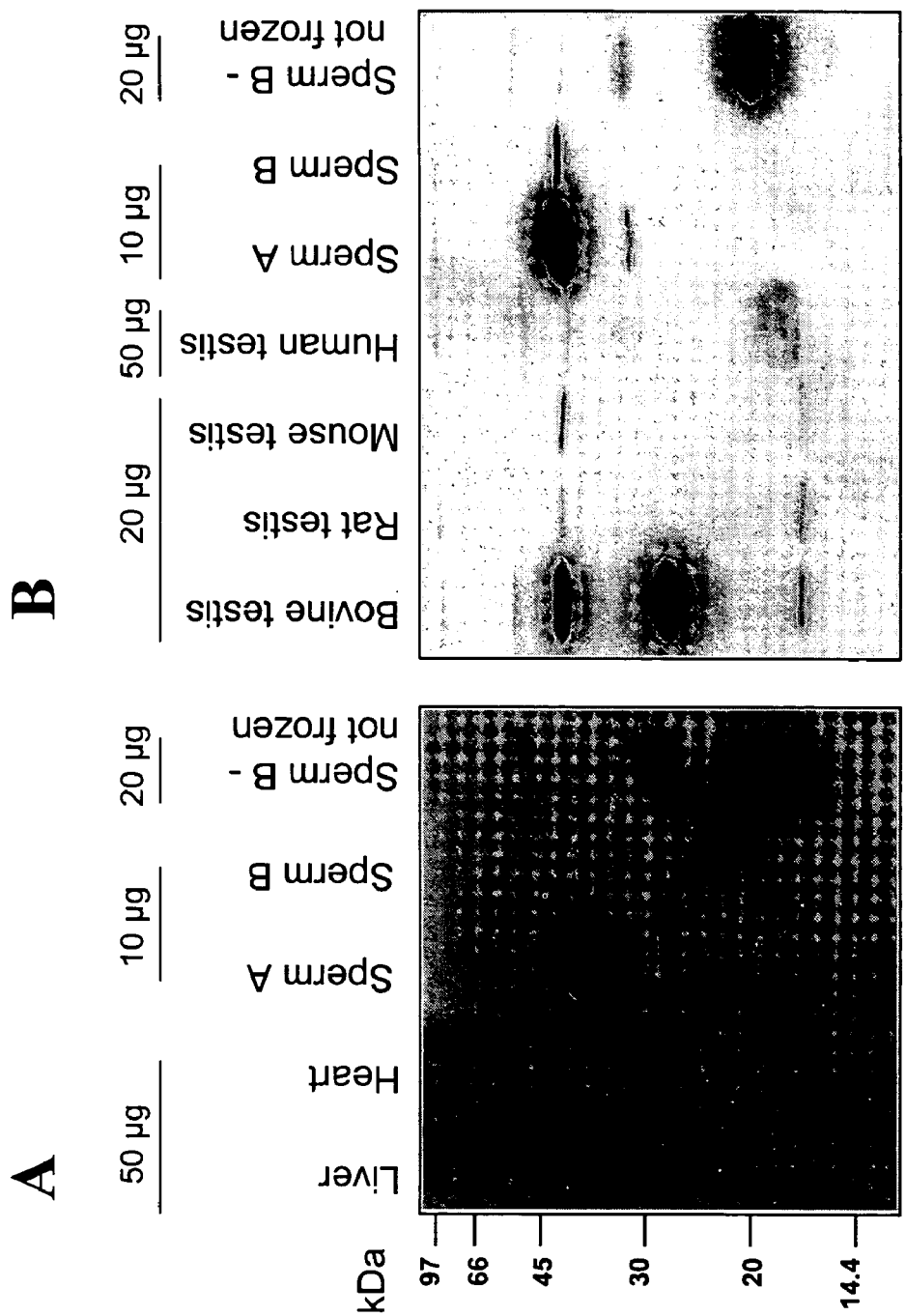
FIGS. 6A-B.

To further corroborate the cell-type restricted expression of Sptrx-3, the inventors performed Western blot analysis in elutriated germ cells from rat testis. Using western blots, Sptrx-3 was detected as a discrete band of 24 kDa in spermatocytes and spermatids while it was absent in other testicular cells such as Leydig, Sertoli or spermatogonia. However, signal is also obtained in mature spermatozoa, which is the result of Sptrx-3 accumulation in the cytoplasmic droplet. Interestingly, the molecular weight of 24 kDa of the protein recognized by the Sptrx-3 antibodies in elutriated rat cells is bigger than the theoretical one predicted on the basis of its amino acid composition. Western blots on bovine testis extracts also showed a major band around 24 kDa, whereas weaker ones appear at 40 kDa and at 15 kDa, the last one being most probably the band corresponding to the calculated size (FIG. 6A). The inventors ruled out the possibility that the upper bands might be a consequence of no-specific cross-reactivity of the antibodies with proteins other than Sptrx-3 as no labeling was obtained when using human liver and heart extracts as negative controls in western blots (FIG. 6B). Thus, the appearance of more than one band suggested either post-translational modification or aggregation of Sptrx-3 protein. Sptrx-3 localization in close association with Golgi suggested that glycosilation might be the most likely posttranslational modification of Sptrx-3. However, pretreatment of testis and sperm extracts with both N- and O-glycosidases did not modify the banding pattern. Surprisingly, support for the aggregation hypothesis came from the use of freshly obtained spermatozoa where a major band of 15 kDa was obtained whereas the same sample subjected to freezing/thawing treatment resulted in the appearance of bands of 24 and 40 kDa coinciding with the disappearance of the original band of 15 kDa (FIG. 6).

Example 5

Expression of Recombinant Sptrx-3 and Enzymatic Activity Assays

Thioredoxins are considered as general protein disulfide reductases and their enzymatic activity can be easily determined spectrophotometrically as a function of the capacity of thioredoxin to reduce the disulfide bonds of insulin using NADPH and thioredoxin reductase (Bjornstedt et al., 1995). To evaluate whether human Sptrx-3 is able to act as reducing agent in vitro, the inventors attempted the expression of recombinant Sptrx-3 in bacteria, using three different tags: Histidine, GST (Glutathione S-transferase), and MBP (maltose binding protein). Each of the three approaches rendered enough soluble protein to carry out enzymatic assays. In contrast, the expression of recombinant Sptrx-3 without any tag also resulted in very low yielding, mostly insoluble. Human Sptrx-3 was then expressed in HEK 293 cells using a bidirectional promoter that simultaneously produces green fluorescent protein as a transfection efficiency control. As shown in FIG. 7, cell extracts of Sptrx-3 overproducing cells did not result in increased activity over the corresponding control extracts transfected with the empty vector (only expresses the green fluorescent protein) or untransfected cells, respectively. However, a positive control overexpressing human TRX-1 resulted in a two-fold increase in enzymatic activity.

Example 6

Sptrx-3 is Over-Expressed in Spermatozoa of Infertile, Teratospermic Men

After characterization of Sptrx-3 expression and localization under physiological conditions throughout spermatogenesis, the possibility that Sptrx-3 expression might be impaired under pathological conditions was investigated. With that purpose Sptrx-3 expression was first investigated in infertile men.

Figure 8A:
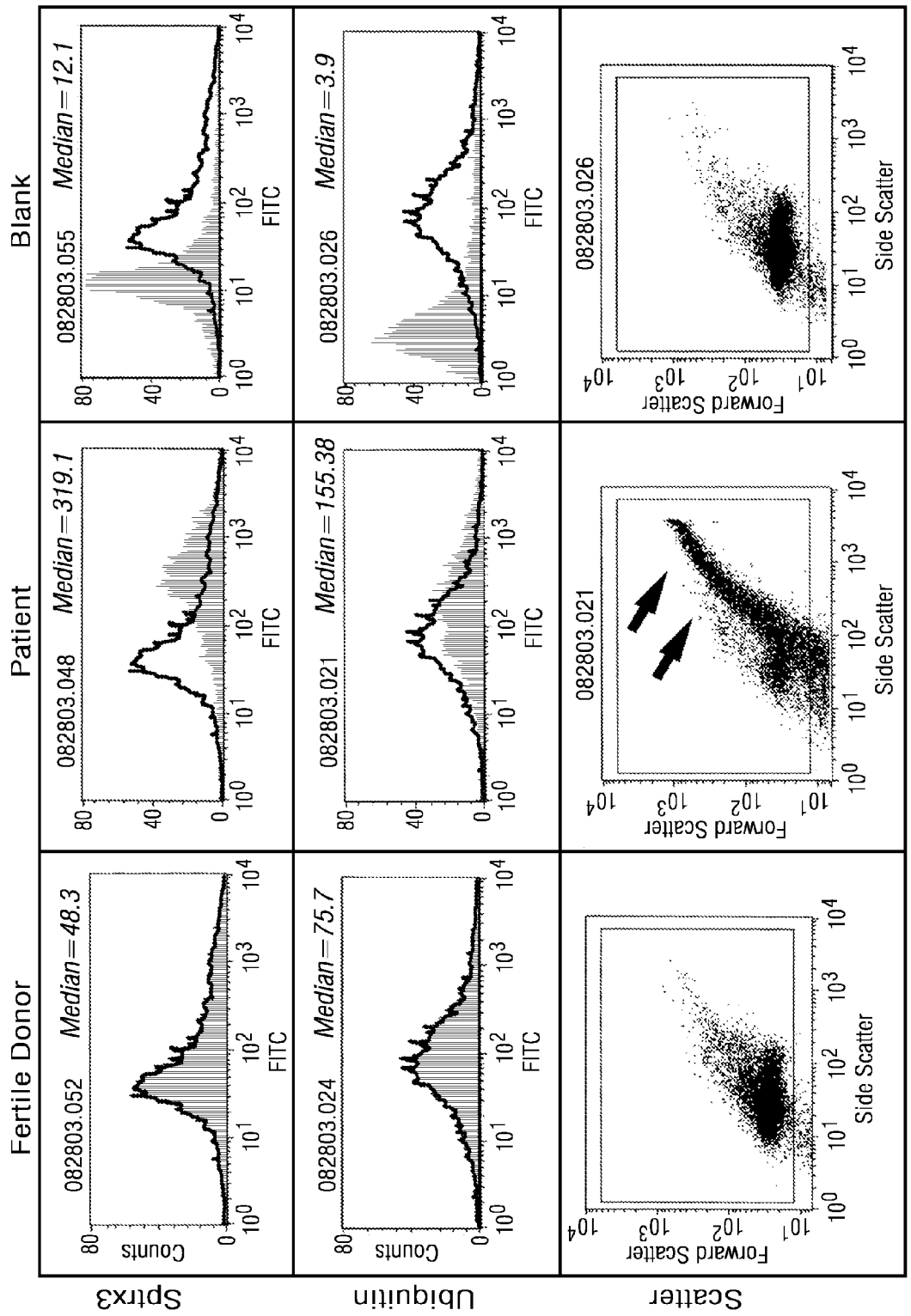

Relative levels of Sptrx-3 in semen of 19 infertile, teratospermic men (further 'patients') and 5 fertile donors (further 'donors') were compared by flow cytometry in the same trial with the co-detection of ubiquitin, an established marker of sperm abnormalities (Rawe et al., 2002; Sutovsky et al., 2001). The average median value of Sptrx-3 induced fluorescence (FIG. 8), a relative measure of positive immune reaction in samples, was 55.3±8.7 for fertile donors, while it was three times higher (168.7±20.0) in infertility patients. Such high Sptrx-3 levels in teratospermic samples were reflected by increased sperm ubiquitin-immunoreactivity: average ubiquitin median values were 139.2±11.7 in patients and 64.1±13.1 in fertile donors. As results of co-expression of ubiquitin and Sptrx-3, there was a strong positive correlation between their respective flow cytometric medians (r=0.85; p<0.0001). These differences in the sperm content of Sptrx-3 (FIG. 8B, FIG. 8C) and ubiquitin (FIG. 8D, FIG. 8E) between patients and fertile donors were readily identified when the samples of some donors (FIG. 8B, FIG. 8D) and patients (FIG. 8C, FIG. 8E), processed for flow cytometric analysis, were pre-screened using epifluorescence microscopy. In general, the samples in the above cohort of 19 infertile donors were characterized as teratospermic, with <8% normal spermatozoa in ejaculated by strict criteria. Some of the samples displayed defined anomalies such as nucleomalasia, round head sperm syndrome (globozoospermia), acrosomal hypoplasia and flagellar pathology (fibrous sheath hypoplasia/stomp tail syndrome). However, basal levels of Sptrx-3 expression were also detected in samples of 5 fertile donors with >40% normal spermatozoa, suggesting that Sptrx-3 levels in human semen increase gradually with the increased content of defective spermatozoa.

Example 7

Sptrx-3 is a Post-Obstruction Sperm Autoantigen.

Similar to teratospermy (poor sperm quality), the development of autoimmune antibodies to spermatozoa is a major concern in reproductive medicine, as it may result in male infertility. Components of the sperm accessory structures are detected frequently as autoantigens in screens of sperm proteins with post-obstruction sera in post-obstructive azoospermia due to vasectomy or heritable defects (Flickinger et al., 2001). Since Sptrx-3 is localized in the sperm acrosome and rat Sptrx-2 was recently found to be a sperm autoantigen (Miranda-Vizuete et al., 2003), the inventors asked whether Sptrx-3 was also recognized by antibodies in post-obstruction sera generated by performing vasectomies in rats. On 2-D western blots of rat sperm extracts, the region between 16 and 25 kDa (where Sptrx-3 is expected to migrate based on the western analysis described above) was strongly stained both by anti-Sptrx-3 serum and by post-vasectomy sera. Co-migration of protein spots stained by anti-Sptrx-3 and by post-vasectomy sera supports the hypothesis that Sptrx-3 was an auto- and/or iso-antigen in rats. FIG. 9 shows two dimensional (2-D) western blots of rat sperm proteins stained with anti-SPTRX-3 serum or post vasectomy rat sera.

Example 8

Sptrx-3 is Expressed at Pre-Invasive Stages of Testicular Tumors

Sptrx-3 expression is seen in CIS (carcinoma in situ) cells, intratubular seminoma cells and microinvasive seminoma cells, but not in invasive seminoma (apart from a few positive cells, less than 1%, in some seminomas). Interestingly there is no positive reaction in intratubular non-seminoma (which shows the histology of embryonic carcinoma) and all other histologies of germ cell tumors (yolk sac, teratoma, choriocarcinoma). All these results from Sptrx-3 staining were also verified using double staining for Sptrx-3 and Plap, which stains pre-invasive germ cell tumor cells such as CIS and gonadoblastoma. The interpretation of these results indicates that Sptrx-3 is expressed in early stages of testicular tumor development. This expression disappears or is down-regulated in more invasive and differentiated testicular tumors.

Acquisition of a novel function for Sptrx-3 must be dependent on testis-specific cofactors or thioredoxin reductases other than cytosolic TrxR1: similar to experience with SPTRX-2 (Miranda-Vizuete et al., 2003; Sadek et al., 2001), no activity in the thioredoxin activity assay was observed when using crude extracts of Sptrx-3 over-expressing cells. In this regard, two different TrxR5 might fulfill this function: TGR, the fusion protein of glutaredoxin-like and thioredoxin reductase domains (Sun et al., 2001) or a novel testis-specific splicing variant of TrxR1 which adds an extra N-terminal glutaredoxin domain.

Acrosomal biogenesis starts during initial steps of spermiogenesis, when the acrosomal vesicle is formed from the Golgi-derived proacrosomal granules (Abou-Haila and Tulsiani, 2000). Here the inventors show that Sptrx-3 expression in rat starts in pachytene spermatocytes and is associated with the Golgi apparatus and proacrosomal granules. In humans and mice, pachytene spermatocyte stage marks the beginning for the synthesis of many acrosome-specific proteins (Ramalho-Santos et al., 2002), most of them following the classical exocytotic pathway. Proteins aimed to follow this pathway usually have a hydrophobic stretch of residues at the N-terminus which can act as a signal motif (Blobel, 2000). However, despite Sptrx-3 expression pattern being coincidental with other acrosome-specific proteins, it lacks a clear signal sequence to follow the ER/Golgi pathway. A leaderless pathway independent of ER/Golgi has been proposed for other proteins including Trx-1 (Nickel, 2003; Rubartelli et al., 1992) but Sptrx-3 is not expected to follow that pathway because Sptrx-3 localizes in the Golgi apparatus. Interestingly, it has been shown recently that the acylation with fatty acids at two Cys residues is responsible for the Golgi localization of GCP16 protein (Ohta et al., 2003). As shown above, additional cysteines are present in the testis-specific exon V of Sptrx-3. Taken together, the Cys-acylation may serve as the signal for Sptrx-3 translocation into the Golgi apparatus. Nevertheless, a translational modification such as acylacion does not explain the apparent gel-shifting of Sptrx-3 in western-blot experiments. Moreover, such behavior is only noted after a freeze-thawing treatment, so detection of a higher band is more likely due to the aggregation of the protein.

Apart from sperm-specific thioredoxins, other redox proteins including peroxiredoxin 1, peroxiredoxin 4 and peroxiredoxin 6 were found to be highly expressed during spermatogenesis (Fujii et al., 2001; Sasagawa et al., 2001). Peroxiredoxin 4 has been proposed to be involved in acrosome biogenesis (Sasagawa et al., 2001) following an expression pattern resembling that of Sptrx-3. Thus, it seems reasonable to hypothesize that Sptrx-3 could also participate in the biogenesis of the acrosome, but further experiments such as genomic knock out will be important to determine the exact role of Sptrx-3 in spermiogenesis.

The above findings regarding normal spermatogenesis show that Sptrx-3 is exclusively expressed during a short period of spermiogenesis. In mature epididymal spermatozoa, Sptrx-3 is found at the cytoplasmic droplet, where the remnants of the cytoplasm and organelles are discarded from the sperm cell after completion of its function. However, in some teratospermic patients Sptrx-3 expression pattern becomes altered as Sptrx-3 is over-expressed and can be easily detected at high levels in the nuclear vacuoles and in the superfluous cytoplasm of morphologically abnormal spermatozoa. Thus, over-expression or retention of Sptrx-3 in mature spermatozoa represents a novel phenotype marker of male infertility as well as a potential target for developing diagnostic assays and drugs.

Example 8

STIX Fertility Test Kit

In this Example, a fertility test kit ("STIX Fertility Test Kit") was produced that allows for the testing of male fertility based upon the evaluation of expression of Sptrx-3. Variations to the fertility test kits provided in this Example are possible and will be recognized by one of skill in the art.

The fertility test kit can detect defective sperm cells. Sperm cells are produced in the testis from sperm precursor cells, spermatids. Like other cells, sperm precursor cells are composed of a nucleus containing chromosomes/DNA, and cytoplasm with supporting structures & molecules. Normal (healthy) sperm can shed their cytoplasm and retain their DNA/chromosomes; however defective sperm fail to shed their cytoplasm. The assay provided in the fertility test kit detects the Sptrx-3 protein in the redundant, retained cytoplasm of defective sperm. A working kit was produced and has been tested on human sperm samples.

The procedure for using the kit is very simple and takes approximately 70 minutes. The STIX Fertility Test Kit may contain: solution #1 (a fixative solution), solution #2 (containing a first antibody), solution # 3 (containing a second antibody), 5 microscopy slides, 5 coverslips, and a tube of mounting medium.

The procedure for using the above kit is as follows:
STEP 1: Add SOLUTION #1 (a fixative solution) to sperm. Allow to sit for 10 min.
STEP 2: Spread 50 microliters of sperm+SOLUTION #1 on a microscopy slide. Allow to dry for 5 min
STEP 3: Add SOLUTION #2 (containing a first antibody) to dry sperm on slide. Allow to sit for 30 min. Dip in water
STEP 4: Add SOLUTION #3 (containing a second antibody) to sperm. Allow to sit for 30 min. Dip in water.
STEP 5: Cover the slide with a microscopy coverslip.
STEP 6—Observe and score+/−signal in 100 cells.

The STIX Fertility Test Kit has several significant advantages. Currently, physicians often pay approximately $150 or more and wait for several weeks to have one sample from one patient tested by a SCSI reference laboratory. However, using the STIX Fertility Test Kit, it is possible to test 10 patients in the physician's own office or andrology laboratory for the same amount of money and get an immediate, more accurate diagnosis of male infertility. Thus, the STIX Fertility Test Kit is accurate, cheap, and may be performed in a doctor's office. This assay (using the STIX Fertility Test Kit) recognizes DNA/chromatin abnormalities but also other sperm abnormalities not related to DNA damage. It has also been estimated that the STIX Fertility Test Kit is very affordable (~$15/assay if a Ten Assay Kit is used; $150/Ten Assay Kit).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,367,110
U.S. Pat. No. 4,393,075
U.S. Pat. No. 4,452,901
U.S. Pat. No. 4,668,621
U.S. Pat. No. 4,683,195
U.S. Pat. No. 4,683,202
U.S. Pat. No. 4,708,964
U.S. Pat. No. 4,761,403
U.S. Pat. No. 4,800,159
U.S. Pat. No. 4,883,750
U.S. Pat. No. 4,946,773
U.S. Pat. No. 5,232,941
U.S. Pat. No. 5,279,721
U.S. Pat. No. 5,310,959
U.S. Pat. No. 5,326,785
U.S. Pat. No. 5,670,360
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,861,268
U.S. Pat. No. 5,861,268
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,876,969
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,928,654
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,099,834
U.S. Pat. No. 6,194,176
U.S. Pat. No. 6,217,875
U.S. Pat. No. 6,486,181
U.S. Pat. No. 6,521,424
U.S. Pat. No. 6,541,519
U.S. Pat. No. 6,558,924
U.S. Pat. No. 6,589,758
U.S. Patent Prov. 60/447,675

Abbondanzo et al., *Breast Cancer Res. Treat.*, 16:182(151), 1990
Abou-Haila, and Tulsiani, *Arch. Biochem. Biophys.*, 379:173-182, 2000.
Allred et al., *Breast Cancer Res. Treat.*, 16:182(149), 1990
Althouse et al., *Theriogenology*, 50:535, 1998.
Altschul and Koonin, *Trends Biochem. Sci.*, 23:444-7, 1998.
Amann, *J. Androl.*, 10:89-98, 1989.
Baccetti et al., *J. Submicrosco. Cytol. Pathol.*, 28:587-596, 1996.
Ballachey et al., *Biol. Reprod.*, 36:915-925, 1987.
Bellus, *J. Macromol. Sci. Pure Appl. Chem.*, A31(1): 1355-1376, 1994.
Bjornstedt et al., *Methods Enzymol.*, 252:209-219, 1995.
Blobel, *Chembiochem.*, 1:86-102, 2000.
Brash, *J. Biol. Chem.*, 274:23679, 1999.
Brown et al. *Immunol. Ser.*, 53:69-82, 1990.
Capaldi et al., *Biochem. Biophys. Res. Comm.*, 76:425, 1977.
Cho et al., *J. Med. Chem.*, 34:1503, 1991.
Conrad, *Clin Rev Allergy Immunol.*, 17(1-2):71-89, 1999.
Crowther, In: *Methods in Molecule Biology*, Vol. 42, Humana Press; NJ, 1995.
Douglas-Hamilton, *Qual. Assur.*, 4:340-347, 1995.
Drobnis, In: *Fertility and reproductive failure*, Scialli and Zinaman (Eds.), Pergamon, N.Y., 77-132, 1992.
Eliason, In: *Current Topics in Andrology*, Matson (Ed.), Ladybrook Publishing, Perth, 2003.
Eliason, In: *The Testis*, Burger and de Kretser (Eds.), Raven Press, NY, 381-399, 1981.

Engvall and Perlmann, *Immunochem.*, 8:871-873, 1971.
Engvall, *Lancet*, 2(8000):1410, 1976.
Engvall, *Med. Biol.*, 55(4):193-200, 1977.
Engvall, *Methods Enzymol*, 70(A):419-39, 1980.
European Appln. 320 308
European Appln. 329 822
Evenson et al., *Hum. Reprod.*, 14:1039-1049, 1999.
Evenson et al., *J. Histochem. Cytochem.*, 30:279-280, 1982.
Ferrari et al., *Andrologia*, 30:85-89, 1998.
Feussner and Wasternack, *Annu. Rev. Plant Biol.*, 53:275, 2002.
Flickinger et al., *Biol. Reprod.*, 64:1451-1459, 2001.
Flickinger et al., *J. Reprod. Immunol.*, 43:35-53, 1999.
Fritsch et al., *Acta Biol. Med. Ger.*, 38:1315, 1979.
Frohman, In: *PCR Protocols: A Guide To Methods And Applications*, Academic Press, N.Y., 1990.
Fujii et al., *Eur. J. Biochem.*, 268:218-225, 2001.
Garner et al., *Mol. Reprod. Dev.*, 53:222-229, 1999.
GB Appln. 2 202 328
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Gripenberg et al., *Scand J. Immunol.*, 7(2):151-157, 1978.
Grüllich et al., *FEBS Lett.*, 489:51, 2001.
Guzick et al., *N. Engl. J. Med.*, 345:1388-1393, 2001.
Hammarström, *Biochem. Biophys. Acta*, 487:517-519, 1977.
Harlow and Lane, In: *Antibodies, a Laboratory Manual*, Cold Spring Harbor Laboratory, 139-281, 1988.
Holmgren, *Methods Enzymol.*, 107:295-300, 1984.
Hope et al., *Biochem. Pharmacol.*, 32:367, 1983.
Hughes et al., *Mutagenesis*, 14:71-75, 1999.
Innis et al., *Proc. Natl. Acad. Sci. USA*, 85(24):9436-9440, 1988.
Invernizzi et al., *J. Biotechnol.*, 109(1-2):169-178, 2004.
Jimenez et al., *J. Biol. Chem.*, 279(33):34971-82, 2004.
Jorgensen et al., *Int. J. Androl.*, 20:201-208, 1997.
Kimura et al., *Biochem. Biophys. Acta*, 922:278, 1987.
Kliewer et al., *Cell*, 83:813-819, 1995.
Kohler and Milstein, *Eur. J. Immunol.*, 6:511-519, 1976.
Kohler and Milstein, *Nature*, 256:495-497, 1975.
Kong et al., *Nat. Genet.*, 31:241-247, 2002.
Koshihara et al., *Biochem. Biophys. Acta*, 792:92, 1984.
Krause, *Hum. Reprod.*, 1:60-66, 1995.
Kruger et al., *Urology*, 30:248-251, 1987.
Kubo et al., *Chem. Pharm. Bull.*, 32:2724, 1987.
Kwoh et al., *Proc. Natl. Acad. Sci. USA*, 86:1173, 1989.
Lankin et al., *Biomed. Biochim. Acta*, 44:655, 1985.
Lax et al., *Biochim. Biophys. Acta*, 1043:12, 1990.
Lynch and Conery, *Science*, 290:1151-1155, 2000.
Makler et al., *Transfusion*, 21(3):303-312, 1981
Miranda-Vizuete et al., *J. Biol. Chem.*, 278:44874-44885, 2003.
Nakamura et al., In: *Handbook of Experimental Immunology* (4th Ed.), Weir et al. (Eds.), 1:27, Blackwell Scientific Publ., Oxford, 1987.
Nickel, *Eur. J. Biochem.*, 270:2109-2119, 2003.
Ohara et al., *Proc. Natl. Acad. Sci. USA*, 86:5673-5677, 1989.
Ohta et al., *J. Biol. Chem.*, 278(51):51957-51967, 2003.
Oko, *Andrologia*, 30:193-206, 1998.
Oliw and Sprecher, *Biochim. Biophys. Acta*, 1002:283, 1989.
Omina and Hammarström et al., *J. Biol. Chem.*, 255:8023, 1980.
PCT Appln. PCT/US87/00880
PCT Appln. PCT/US89/01025
PCT Appln. WO 84/03564
PCT Appln. WO 88/10315
PCT Appln. WO 89/06700
PCT Appln. WO 90/07641
Ramalho-Santos et al., *Biol. Reprod.*, 67:1043-1051, 2002.
Rawe et al., *Hum. Reprod.*, 17:2119-2127, 2002.
Routzahn and Waugh, *J. Struct. Funct. Genomics*, 2(2):83-92, 2002.
Rubartelli et al., *J. Biol. Chem.*, 267:24161-24164, 1992.
Rybnikova et al., *Eur. J. Neurosc.*, 12:1669-1678, 2000.
Sadek et al., *Genes Cells*, 6:1077-1090, 2001.
Saez et al., *Scand. J. Infect. Dis.*, 35(4):282-4, 2003.
Salari et al., *Prostagland. Leukot. Med.*, 13:53, 1984.
Sambrook et al., In: *Molecular cloning*, Cold Spring Harbor Laboratory Press, Cold Spring Harbor, N.Y., 2001.
Sarngadharan et al., *Princess Takamatsu Symp.*, 15:301-308, 1984.
Sasagawa et al., *Eur. J. Biochem.*, 268:3053-3061, 2001.
Schewe et al., *FEBS Lett.*, 60:149, 1975.
Sekiya and Okuda, et al., *Biochem. Biophys. Res Commun.*, 105:1090, 1982.
Shao et al., *J. Biol. Chem.*, 272:6105-6113, 1997.
Shureiqi et al., *J. Natl. Cancer Inst.*, 92:1136, 2000.
Spyrou et al., *Hum. Genet.*, 109:429-439, 2001.
Spyrou et al., *J. Biol. Chem.*, 272:2936-2941, 1997.
Sun et al., *Biol. Reprod.*, 56:602-607, 1997.
Sun et al., *Proc. Natl. Acad. Sci. USA*, 98:3673-3678, 2001.
Sutovsky et al., *Hum. Reprod.*, 16:250-258, 2001.
Sutovsky et al., *Human Reprod.*, 16:250-258, 2001.
Sutovsky et al., *Mol. Reprod. Dev.*, 61:406-413, 2002.
Uchiki et al., *Anal. Biochem.*, 301(1):35-48, 2002.
van der Schans et al., *J. Androl.*, 21:250-257, 2000.
Walker et al., *Proc. Natl. Acad. Sci. USA*, 89:392-396 1992.
Wollman et al., *J. Biol. Chem.*, 263:15506-15512, 1988.
World Health Organization (WHO)—Laboratory manual for the examination of human semen and semen cervical mucus interaction. Cambridge University Press, Cambridge, 1987, 1992, 1999.
Yamamoto, *Free Radic. Biol. Med.*, 10:149, 1991.
Yoshimoto et al., *Biochem. Biophys. Acta*, 713:470, 1982.
Zhan et al., *Gene*, 281(1-2):1-9, 2001.

What is claimed is:

1. A method of detecting spermatozoa or semen in a sample comprising assaying a sample for the presence of spermatid-specific thioredoxin-3 (Sptrx-3) or a nucleic acid sequence encoding Sptrx-3 according to SEQ ID NO :9, wherein the presence of the Sptrx-3 or nucleic acid sequence is indicative of the presence of spermatozoa or semen in the sample.

2. The method of claim 1 wherein assaying the sample for the presence of Sptrx-3 comprises an enzyme linked immunosorbent assay (ELISA), enzyme-linked coagulation assay (ELCA), Western blotting, radioimmunoassay, immunohistochemical assay, immunocytochemical assay, one- or two-dimensional PAGE, dot blotting, or FACS analysis.

3. The method of claim 1, wherein assaying the sample for the presence of Sptrx-3 comprises:
   combining the sample and an antibody or fragment thereof, wherein the antibody or fragment thereof binds specifically to Sptrx-3 when present in the sample; and
   detecting the antibody or fragment thereof bound to Sptrx-3.

4. The method of claim 3, wherein the antibody or fragment thereof is immobilized on a solid support.

5. The method of claim 3, wherein the antibody or fragment thereof binds immunospecifically to a polypeptide comprising an amino acid sequence of SEQ ID NO: 10.

6. The method of claim 1, wherein assaying the sample for the presence of Sptrx-3 comprises:
   combining the sample, a labeled binding agent, and an antibody or fragment thereof immobilized on a solid support;
   washing the support; and
   detecting labeled binding agent bound to Sptrx-3 bound to antibody or fragment thereof immobilized on the support;
   wherein the antibody or fragment thereof and the labeled binding agent each bind specifically to Sptrx-3 when present in the sample.

7. The method of claim 1, wherein the sample is a fluid sample.

8. The method of claim 1, wherein the sample is a sample from a human subject.

9. The method of claim 1, further comprising: obtaining a source sample suspected of containing spermatozoa or semen; isolating protein or polypeptide from the source sample to form an analytical sample; and assaying the analytical sample for the presence of Sptrx-3.

* * * * *